US012747479B2

(12) United States Patent
Chiu et al.

(10) Patent No.: US 12,747,479 B2
(45) Date of Patent: Sep. 29, 2026

(54) COMPOSITIONS AND METHODS FOR DETECTION OF MALARIA

(71) Applicant: Roche Molecular Systems, Inc., Pleasanton, CA (US)

(72) Inventors: Sharon Ho-Chen Chiu, Pleasanton, CA (US); Yvonne Gicheru, Mountain House, CA (US); Marintha Heil, Danville, CA (US); Michael K. Lee, San Ramon, CA (US); Chitra Manohar, San Ramon, CA (US); Rochak Mehta, Fremont, CA (US); Ellen Ordinario, Oakland, CA (US); Jaya Rajamani, Pleasanton, CA (US); Jingtao Sun, San Ramon, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 596 days.

(21) Appl. No.: 18/255,235

(22) PCT Filed: Dec. 3, 2021

(86) PCT No.: PCT/EP2021/084099

§ 371 (c)(1),
(2) Date: May 31, 2023

(87) PCT Pub. No.: WO2022/117784

PCT Pub. Date: Jun. 9, 2022

(65) Prior Publication Data

US 2024/0102110 A1 Mar. 28, 2024

Related U.S. Application Data

(60) Provisional application No. 63/121,338, filed on Dec. 4, 2020.

(51) Int. Cl.
*C12Q 1/68* (2018.01)
*C12Q 1/6818* (2018.01)
*C12Q 1/6893* (2018.01)

(52) U.S. Cl.
CPC ......... *C12Q 1/6893* (2013.01); *C12Q 1/6818* (2013.01); *C12Q 2600/16* (2013.01)

(58) Field of Classification Search
None
See application file for complete search history.

(56) References Cited

U.S. PATENT DOCUMENTS

2017/0073738 A1 3/2017 Fischer et al.

FOREIGN PATENT DOCUMENTS

| | | | | |
|---|---|---|---|---|
| JP | 2012519472 | A | 8/2012 | |
| WO | WO-2006088895 | A2 * | 8/2006 | .......... C12Q 1/6806 |
| WO | WO-2008146938 | A1 * | 12/2008 | ............. A61P 33/02 |
| WO | 2020132408 | A2 | 6/2020 | |
| WO | 2023/079032 | A1 | 5/2023 | |

OTHER PUBLICATIONS

Seilie et al. Am. J. Trop. Med. Hyg., 100(6), 2019, pp. 1466-1476, including supplemental materials; 34 pages total (Year: 2019).*

International Searching Authority, International Search Report, for International Patent Application No. PCT/EP2021/084099 (Jun. 9, 2022).

International Searching Authority, Written Opinion of the International Searching Authority, for International Patent Application No. PCT/EP2021/084099 (Jun. 9, 2022).

Mathieu Rougemont, et al., "Detection of Four Plasmodium Species in Blood from Human by 18S rRNA Gene Subunit-Based and Species-Specific Real-Time PCR Assays," Journal of Clinical Microbiology 42(12):5636-4643 (2004).

Divis et. al. Malaria Journal, A taqMan real-time PCR assay for the detection and quantitation of Plasmodium knowlesi, 2010, pp. 1-7.

Lefterova et. al., Journal of Clinical Microbiology, Simple Real-Time PCR and Amplicon Sequencing Method for Identification of Plasmodium Species in Human Whole Blood, 2015, pp. 2251-2257, vol. 53 No. 7.

Shokoples et. al., Journal of clinical microbiology, Multiplexed real-time pcr assayfor discrimination of plasmodium species with improved sensivity for mixed infections, 2009, pp. 975-980, vol. 47 No. 4.

Whiley et. al., Clinical review in microbiology, False negative results in nucleic acid amplification tests—do we need to routinely use two genetic targets in all assays to overcome problems caused by sequence variation, 2008, pp. 71-76.

* cited by examiner

*Primary Examiner* — Juliet C Switzer
(74) *Attorney, Agent, or Firm* — Eric Grant Lee

(57) ABSTRACT

Methods for the rapid detection of the presence or absence of Malaria parasites (including *Plasmodium*) in a biological or non-biological sample are described. The methods can include performing an amplifying step, a hybridizing step, and a detecting step. Additionally, the assay can be a multiplex assay, to amplify and detect a plurality of *Plasmodium* targets simultaneously, which offers advantages over singleplex assays. Furthermore, oligonucleotide primers and oligonucleotide probes targeting Malaria parasites (including *Plasmodium*) and kits are provided that are designed for the detection of *Plasmodium*, including, but not limited to, the *Plasmodium* species of *P. falciparum, P. vivax, P. ovale, P. knowlesi*, and *P. malariae*. Also described are kits, reaction mixtures, and oligonucleotides (e.g., primer and probe) for the amplification and detection of Malaria parasites (including *Plasmodium*).

20 Claims, 23 Drawing Sheets

Specification includes a Sequence Listing.

| Target | CT | RFI | Baseline | Slope |
|---|---|---|---|---|
| 18S-1 | 21.1 | 8.0 | 0.9 | -3.14 |
| 18S-3 | 25.3 | 11.3 | 0.9 | -3.10 |
| 18S-4 | 20.3 | 16.2 | 0.8 | -3.06 |
| R125 | 20.7 | 12.6 | 1.4 | -3.12 |
| MT-1 | 26.6 | 12.6 | 2.0 | -3.22 |
| MT-2 | 27.5 | 14.1 | 1.1 | -3.15 |

FIG. 3

| Primer Set | Probe |
|---|---|
| 18S-1 Original | <FAM_Thr>AAGGA<BHQ_2>AGGCAGCAGGCGCGTAAATTACCC<Spc_C3> |
| 18S-1 Redesign | <FAM_Thr>AGGCA<BHQ_2>GCAGGCGCGTAAATTACCCAA<Spc_C3> |

| Target | Copies/uL in P&E of 1:$10^5$ Culture Dilution |
|---|---|
| 18S-1 | 16100 |
| 18S-3 | 510 |
| 18S-4 | 16380 |
| R125 | 6230 |
| MT-1 | 81 |
| MT-2 | 28 |

FIG. 5

| FAM Channel | Multiplex | | | 18S-1+GIC | | | 18S-4+GIC | | |
|---|---|---|---|---|---|---|---|---|---|
| | CT | RFI | Baseline | CT | RFI | Baseline | CT | RFI | Baseline |
| 1:10$^4$ Dilution | 19.2 | 16.5 | 1.8 | 19.2 | 22.8 | 1.2 | 19.2 | 9.9 | 1.0 |
| 1:10$^5$ Dilution | 22.7 | 16.2 | 1.8 | 22.8 | 22.2 | 1.3 | 22.6 | 10.0 | 1.1 |
| 1:10$^6$ Dilution | 26.5 | 14.0 | 1.8 | 26.3 | 20.2 | 1.2 | 25.8 | 9.0 | 1.0 |
| 1:10$^7$ Dilution | 29.6 | 9.0 | 1.7 | 29.7 | 15.5 | 1.2 | 28.6 | 5.9 | 1.1 |
| Slope | -3.5 | | | -3.5 | | | -3.14 | | |

FIG. 6A

| FAM Channel | Multiplex | | | 18S-1+GIC | | | R125+GIC | | |
|---|---|---|---|---|---|---|---|---|---|
| | CT | RFI | Baseline | CT | RFI | Baseline | CT | RFI | Baseline |
| 1:10$^4$ Dilution | 19.4 | 20.1 | 2.1 | 20.0 | 25.8 | 1.2 | 19.1 | 15.2 | 1.4 |
| 1:10$^5$ Dilution | 22.8 | 19.3 | 1.8 | 23.6 | 25.0 | 1.2 | 22.6 | 14.9 | 1.5 |
| 1:10$^6$ Dilution | 26.4 | 17.2 | 1.8 | 27.2 | 22.4 | 1.3 | 26.0 | 14.3 | 1.4 |
| 1:10$^7$ Dilution | 29.6 | 11.8 | 2.0 | 30.7 | 17.7 | 1.2 | 29.3 | 13.7 | 1.3 |
| Slope | -3.4 | | | -3.6 | | | -3.4 | | |

FIG. 7A

| IVT copies | Multiplex | | | | | | 18S-1+GIC | | | R125+GIC | | |
|---|---|---|---|---|---|---|---|---|---|---|---|---|
| | 18S-1 CT | 18S-1 RFI | 18S-1 Baseline | R125 CT | R125 RFI | R125 Baseline | CT | RFI | Baseline | CT | RFI | Baseline |
| $10^5$ | 20.2 | 13.9 | 2.2 | 19.2 | 8.4 | 2.1 | 20.2 | 25.1 | 1.0 | 19.5 | 14.1 | 1.3 |
| $10^4$ | 23.7 | 11.9 | 2.5 | 22.7 | 8.2 | 2.3 | 23.9 | 24.1 | 1.1 | 23.0 | 13.4 | 1.4 |
| $10^3$ | 27.2 | 10.8 | 2.5 | 26.1 | 7.5 | 2.5 | 27.4 | 21.3 | 1.2 | 26.3 | 12.8 | 1.5 |
| $10^2$ | 30.3 | 7.7 | 2.3 | 29.2 | 6.6 | 2.4 | 30.6 | 14.5 | 1.1 | 29.7 | 11.3 | 1.4 |
| 10 | 32.2 | 3.4 | 2.3 | 32.4 | 4.2 | 2.5 | 32.6 | 5.5 | 1.2 | 32.3 | 9.2 | 1.4 |
| Slope | -3.4 | | | -3.3 | | | -3.5 | | | -3.4 | | |

FIG. 8

| Input | | Multiplex 18S + R125 | | |
|---|---|---|---|---|
| | | CT | RFI | Baseline |
| *P. falciparum* | 1:10$^4$ Dilution | 27.44 | 17.01 | 1.11 |
| | 1:10$^5$ Dilution | 30.80 | 14.58 | 1.18 |
| | 1:10$^6$ Dilution | 33.56 | 9.21 | 1.06 |
| | 1:10$^7$ Dilution | 35.68 | 3.73 | 1.01 |

FIG. 10A

COMPOSITIONS AND METHODS FOR DETECTION OF MALARIA

CROSS-REFERENCE TO RELATED APPLICATIONS

This patent application is the U.S. national stage application of International Patent Application No. PCT/EP2021/084099, filed Dec. 3, 2021, which claims priority to U.S. Provisional Patent Application No. 63/121,338, filed Dec. 4, 2020, the contents of both of which are incorporated herein by reference in their entireties.

FIELD OF THE INVENTION

The present disclosure relates to the field of in vitro diagnostics. Within this field, the present invention concerns the amplification and detection of a target nucleic acid that may be present in a sample and particularly, the amplification, detection, and quantitation of a target nucleic acid comprising sequence variations and/or individual mutations of Malaria parasites, using primers and probes. The invention further provides reaction mixtures and kits containing primers and probes for amplification and detection of Malaria.

BACKGROUND OF THE INVENTION

Malaria is a mosquito-borne infectious disease that affects humans and other animals. Malaria is a disease caused by the single-celled microorganism *Plasmodium* parasite that is transmitted to humans after being bitten by infected female *Anopheles* mosquitoes. Initial symptoms of Malaria include fever, headache, and chills, and can be treated with available anti-malarial drugs. If left untreated, severe Malaria can develop, with symptoms including anemia, cerebral malaria, and respiratory distress, which can ultimately result in death.

According to the 2018 World Health Organization (WHO) Report, roughly 3.2 billion people are at risk for Malaria, across 87 countries, which are primarily located in tropical and subtropical regions. There are roughly 219 million cases of Malaria per year, with 92% of those cases coming from Africa, 5% in Southeast Asia, and 2% in East Mediterranean countries. The U.S. presents with about 1,700 cases per year. Malaria also results in 435,000 fatalities a year, with 266,000 of those fatalities striking children under five years old. Efforts to eradicate and prevent Malaria are ongoing, which include insecticide-treated nets, increasing patient access to healthcare, drug development vaccines, and genetically-modified mosquitoes (GMO). Although the U.S. is not considered an endemic country for Malaria, global travel to/from the U.S. may lead to an increase in cases of imported Malaria.

There are at least five species of *Plasmodium* that are known to infect humans: *P. falciparum, P. vivax, P. ovale, P. malariae*, and *P. knowlesi*. Clinical presentations can vary, depending on the species of *Plasmodium. P. falciparum* is the most deadly species, which has been known to cause rapid cell division in infected red blood cells, which causes anemia and blocked blood vessels to the brain. The *Plasmodium* life cycle is complex, with the parasite alternating between sexual reproduction in the mosquito and asexual reproduction in the human host. This life cycle is shown in the FIG. 1, which was taken from the CDC website (https://www.cdc.gov/malaria). Symptoms are caused by the parasite during the blood stages and can appear between 7-30 days after a mosquito bite. *P. vivax* and *P. ovale* can remain dormant in the liver stage, re-activating months or even years later.

With respect to blood supply and blood donations, there already exists major challenges to maintain sufficient blood supply with critical shortages in the Southern and Eastern U.S. Malaria presents an additional problem for blood supply and blood donations. For example, while the U.S. is considered a non-endemic country, global travel may lead to an increase in the cases of imported Malaria, thereby affecting the blood supply in the U.S. Worldwide, the current strategies regarding Malaria employed to maintain safety of blood supply include: (1) Selective Testing, and (2) Donor Deferral, with the U.S. following a Donor Deferral policy. Typically, donors are deferred based on responses to the screening questionnaire, based on history, residence, and travel. In the U.S., an estimated 191,000 donors are temporarily deferred (1-3 years) with the majority of deferrals attributed to traveling to endemic areas. Moreover, deferred donations negatively impact the blood supply, because roughly only ¼ of donors who are temporarily deferred actually return for subsequent blood donation after the deferral period has concluded. Donor deferrals negatively impact the blood supply by excluding donations based on questionnaire answers, regardless of Malaria status. On the other hand, selective testing reduces the impact on blood supply inventory as compared to donor deferral. Selective testing of blood donations is also based on questionnaire responses, but the selective testing policy allows for shorter deferral times and reinstatement of donors depending on donor's Malaria status. In countries that have selective testing policy, testing is done by enzyme immunoassays. At least three countries have implemented testing of Malaria in blood donations: France, England, and Australia. In France, of the 3 million donations one year, about 180,000 donations were tested, and of those 180,000 tested donations, about 3,300 (or 1.8%) were positive. Several diagnostic and screening methods exist for Malaria. Detection of Malaria by microscopy of Giemsa-stained blood smears allows for species identification, is inexpensive, and remains the gold standard. However, microscopy is not capable of high throughput screening/detection. Rapid Diagnostic Tests (RDT) that employ methods for immunochromatographic detection of Malaria antigens are fast and inexpensive, but exhibit low sensitivity (200-5,000 p/μL) and still require confirmation by microscopy. Enzyme Immunoassays (EIA) that detect anti-*Plasmodium* antibodies in serum are widely used, but exhibit low sensitivity as well. By contrast, nucleic acid tests (NAT) are suitable for high throughput screening/detection and are highly sensitive (<1 p/μL). Thus, nucleic acid tests represent the best way to detect and screen for blood samples for Malaria, owing to its high sensitivity and high throughput capabilities. However, at present, there are no in vitro diagnostic nucleic acid tests available for screening blood donations. Thus, there is a need in the art for a quick, reliable, specific, and sensitive method for detecting and quantifying the presence of Malaria in biological samples, such as blood.

In the field of molecular diagnostics, the amplification and detection of nucleic acids is of considerable significance. Such methods can be employed to detect any number of microorganisms, such as viruses and bacteria. The most prominent and widely-used amplification technique is the Polymerase Chain Reaction (PCR). Other amplification techniques include Ligase Chain Reaction, Polymerase Ligase Chain Reaction, Gap-LCR, Repair Chain Reaction, 3SR, NASBA, Strand Displacement Amplification (SDA), Transcription Mediated Amplification (TMA), and Qβ-amplification. Automated systems for PCR-based analysis often make use of a real-time detection of product amplification during the PCR process in the same reaction vessel. Key to such methods is the use of modified oligonucleotides carrying reporter groups or labels.

The absence of a reliable, quick, inexpensive, and sensitive means for detecting Malaria, threatens the safety of the blood donor supply. Therefore, there is a need in the art for a quick, reliable, specific, and sensitive method for detecting and quantifying the presence of Malaria in biological samples, such as blood. This present disclosure is directed to a polymerase chain reaction (PCR)-based assay to detect and screen *Plasmodium* spp (*P. falciparum, P. vivax, P. ovale, P. knowlesi*, and *P. malariae*) in blood samples and donations.

SUMMARY OF THE INVENTION

The instant patent application contains a Sequence Listing, which has been submitted electronically in XML format and is hereby incorporated by reference in its entirety. The XML copy, created May 23, 2023, is named "35951-US_Sequence_Listing," and is 75,000 bytes in size.

The present disclosure relates to methods for the rapid detection of the presence or absence of Malaria parasites (such as *Plasmodium*) in a biological or non-biological sample, for example, multiplex detection and quantitating of Malaria parasites (such as *Plasmodium*) by real-time polymerase chain reaction (PCR) in a single test tube or vessel. Herein, methods of detection of Malaria parasites (such as *Plasmodium*) are disclosed comprising performing at least one cycling step, which may include an amplifying step and a hybridizing step. Furthermore, oligonucleotide primers, oligonucleotide probes, and kits that are designed for the detection of Malaria parasites (such as *Plasmodium*) in a single tube or vessel are provided.

One aspect is directed to a method for detecting one or more Malaria parasite species in a sample, the method comprising: (a) performing an amplification step comprising contacting the sample with one or more set of primers to produce an amplification product, if a target nucleic acid of the one or more Malaria parasite species is present in the sample; (b) performing a hybridization step comprising contacting the one or more probes with the amplification product, if a target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises: (1) a set of primers comprising primers comprising the nucleic acid sequences of SEQ ID NOs:34, 35, and 36, or complements thereof; and a probe comprising the nucleic acid sequence of SEQ ID NO:4, or a complement thereof; and/or (2) a set of primers comprising primers comprising the nucleic acid sequence of SEQ ID NOs:56 and 57, or complements thereof; and a probe comprising the nucleic acid sequence of SEQ ID NO:58, or a complement thereof. In another embodiment, the one or more set of primers and the one or more probes comprises: (1) a set of primers comprising primers comprising the nucleic acid sequences of SEQ ID NOs:34, 35, and 36, or complements thereof; and a probe comprising the nucleic acid sequence of SEQ ID NO:4, or a complement thereof; and (2) a set of primers comprising primers comprising the nucleic acid sequence of SEQ ID NOs:56 and 57, or complements thereof; and a probe comprising the nucleic acid sequence of SEQ ID NO:58, or a complement thereof. In another embodiment, the one or more Malaria parasite species belongs to the genus *Plasmodium*. In another embodiment, the one or more Malaria parasite species that belongs to the genus *Plasmodium* is *P. falciparum, P. vivax, P. ovale, P. malariae*, and/or *P. knowlesi*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In another embodiment, the one or more probes is labeled. In another embodiment, the one or more probes is labeled with a donor fluorescent moiety and a corresponding acceptor moiety. In another embodiment, step (c) further comprises detecting the presence or absence of fluorescent resonance energy transfer (FRET) between the donor fluorescent moiety and the acceptor moiety of the one or more probes, wherein the presence or absence of fluorescence is indicative of the presence of absence of the one or more Malaria parasite species in the sample.

Another aspect is directed to a method for detecting a first target nucleic acid and/or a second target nucleic acid of one or more Malaria parasite species in a sample, the method comprising: (a) performing an amplification step comprising contacting the sample with one or more set of primers to produce an amplification product, if the first target nucleic acid and/or the second target nucleic acid of the one or more Malaria parasite species is present in the sample; (b) performing a hybridization step comprising contacting the one or more probes with the amplification product, if the first target nucleic acid and/or the second target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises: (1) a set of primers and a probe for the first target nucleic acid of the one or more Malaria parasite species, wherein the set of primers comprises primers comprising the nucleic acid sequences of SEQ ID NOs:34, 35, and 36, or complements thereof and wherein the probe comprises the nucleic acid sequence of SEQ ID NO:4, or a complement thereof and (2) a set of primers and a probe for the second target nucleic acid of the one or more Malaria parasite species, wherein the set of primers comprises primers comprising the nucleic acid sequences of SEQ ID NOs:56 and 57, or a complements thereof and wherein the probe comprises the nucleic acid sequence of SEQ ID NO:58, or a complement thereof. Another aspect is directed to a method for detecting one or more Malaria parasite species in a sample, the method comprising: (a) performing an amplification step comprising contacting the sample with one or more set of primers to produce an amplification product, if a target nucleic acid of the one or more Malaria parasite species is present in the sample; (b) performing a hybridization step comprising contacting the one or more probes with the amplification product, if the target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises a set of primers comprising primers comprising the nucleic acid sequences of SEQ ID NOs:34, 35, and 36, or complements thereof and a probe comprising the nucleic acid sequence of SEQ ID NO:4, or a complement thereof. Another aspect is directed to a method for detecting one or more Malaria parasite species in a sample, the method comprising: (a) performing an amplification step comprising contacting the sample with one or more set of primers to produce an amplification product, if a target nucleic acid of the one or more Malaria parasite species is present in the sample; (b) performing a hybridization step comprising contacting the one or more probes with the amplification product, if the target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises a set of primers comprising primers comprising the nucleic acid sequences of SEQ ID NOs:56 and 57, or complements thereof and a probe comprising the nucleic acid sequence of SEQ ID NO:58, or a complement thereof. In a related embodiment, the one or more Malaria parasite species belongs to the genus *Plasmodium*. In another embodiment, the one or more Malaria parasite species that belongs to the genus *Plasmodium* is *P. falciparum, P. vivax, P. ovale, P. malariae*, and/or *P. knowlesi*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In another embodiment, the one or more probes is labeled. In another embodiment, the one or more probes is labeled with a donor fluorescent moiety and a corresponding acceptor moiety.

Another aspect is directed to a kit for detecting one or more Malaria parasite species that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: (1) a set of primers comprising primers comprising the nucleic acid sequences of SEQ ID NOs:34, 35, and 36, or complements thereof; and a probe comprising the nucleic acid sequence of SEQ ID NO:4, or a complement thereof and/or (2) a set of primers comprising primers comprising the nucleic acid sequences of SEQ ID NOs:56 and 57, or complements thereof; and a probe comprising the nucleic acid sequence of SEQ ID NO:58, or a complement thereof. In another embodiment, the one or more set of primers and the one or more probes comprises: (1) a set of primers comprising primers comprising the nucleic acid sequences of SEQ ID NOs:34, 35, and 36, or complements thereof; and a probe comprising the nucleic acid sequence of SEQ ID NO:4, or a complement thereof; and (2) a set of primers comprising primers comprising the nucleic acid sequences of SEQ ID NOs:56 and 57, or complements thereof and a probe comprising the nucleic acid sequence of SEQ ID NO:58, or a complement thereof. In another embodiment, the one or more Malaria parasite species belongs to the genus *Plasmodium*. In another embodiment, the one or more Malaria parasite species that belongs to the genus *Plasmodium* is *P. falciparum, P. vivax, P. ovale, P. malariae*, and/or *P. knowlesi*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In another embodiment, the one or more probes is labeled. In another embodiment, the one or more probes is labeled with a donor fluorescent moiety and a corresponding acceptor moiety. Another aspect is directed to a kit for detecting a first target nucleic acid and/or a second target nucleic acid of one or more Malaria parasite species that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: (1) a set of primers and a probe for the first target nucleic acid of the one or more Malaria parasite species, wherein the set of primers comprises primers comprising the nucleic acid sequences of SEQ ID NOs:34, 35, and 36, or complements thereof; and wherein the probe comprising the nucleic acid sequence of SEQ ID NO:4, or a complement thereof and (2) a set of primers and a probe for the second target nucleic acid of the one or more Malaria parasite species, wherein the set of primers comprises primers comprising the nucleic acid sequences of SEQ ID NOs:56 and 57, or complements thereof; and wherein the probe comprising the nucleic acid sequence of SEQ ID NO:58, or a complement thereof. Another aspect is directed to a kit for detecting one or more Malaria parasite species that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: a set of primers comprising primers comprising the nucleic acid sequences of SEQ ID NOs:34, 35, and 36, or complements thereof; and a probe comprising the nucleic acid sequence of SEQ ID NO:4, or a complement thereof. Another aspect is directed to a kit for detecting one or more Malaria parasite species that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: a set of primers comprising primers comprising the nucleic acid sequences of SEQ ID NOs:56 and 57, or complements thereof and a probe comprising the nucleic acid sequence of SEQ ID NO:58, or a complement thereof. In another embodiment, the one or more Malaria parasite species belongs to the genus *Plasmodium*. In another embodiment, the one or more Malaria parasite species that belongs to the genus *Plasmodium* is *P. falciparum, P. vivax, P. ovale, P. malariae*, and/or *P. knowlesi*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In another embodiment, the one or more probes is labeled. In another embodiment, the one or more probes is labeled with a donor fluorescent moiety and a corresponding acceptor moiety.

In one aspect, a method for detecting a Malaria parasite in a sample is provided, the method comprising: (a) performing an amplification step comprising contacting the sample with one or more set of primers to produce an amplification product, if a target nucleic acid of a Malaria parasite is present in the sample; (b) performing a hybridization step comprising contacting the one or more probes with the amplification product, if a target nucleic acid of a Malaria parasite is present in the sample; and (c) detecting the presence or absence of the amplification product, wherein the presence of the amplification product is indicative of the presence of a Malaria parasite in the sample, and wherein the absence of the amplification product is indicative of the absence of a Malaria parasite in the sample; and wherein the one or more set of primers and the one or more probes comprises: (1) a set of primers comprising a first primer comprising the nucleic acid sequence of SEQ ID NO:34, or a complement thereof, and a second primer comprising the nucleic acid sequence of SEQ ID NO:36, or a complement thereof; and a probe comprising the nucleic acid sequence of SEQ ID NO:4, or a complement thereof and/or (2) a set of primers comprising a first primer comprising the nucleic acid sequence of SEQ ID NO:22, or a complement thereof, and a second primer comprising the nucleic acid sequence of SEQ ID NO:27, or a complement thereof; and a probe comprising the nucleic acid sequence of SEQ ID NO:25, or a complement thereof. In one embodiment, the Malaria parasite belongs to the genus *Plasmodium*. In another embodiment, the Malaria parasite that belongs to the genus *Plasmodium* is *Plasmodium falciparum*. In one embodiment, the sample is a biological sample, such as whole blood, respiratory specimens, urine, fecal specimens, blood specimens, plasma, dermal swabs, nasal swabs, wound swabs, blood cultures, skin, or soft tissue infections. In one embodiment, the biological sample is whole blood. In another embodiment, the one or more probes is labeled. In a related embodiment, the one or more probes is labeled with a donor fluorescent moiety and a corresponding acceptor moiety. In another embodiment, step (c) further comprises detecting the presence or absence of fluorescent resonance energy transfer (FRET) between the donor fluorescent moiety and the acceptor moiety of the one or more probes, wherein the presence or absence of fluorescence is indicative of the presence of absence of a Malaria parasite in the sample.

In one aspect, a method for detecting a first target nucleic acid and a second target nucleic acid of a Malaria parasite in a sample is provided, the method comprising: (a) performing an amplification step comprising contacting the sample with one or more set of primers to produce an amplification product, if the first target nucleic acid and/or the second target nucleic acid of a Malaria parasite is present in the sample; (b) performing a hybridization step comprising contacting the one or more probes with the amplification product, if the first target nucleic acid and/or the second target nucleic acid of a Malaria parasite is present in the sample; and (c) detecting the presence or absence of the amplification product, wherein the presence of the amplification product is indicative of the presence of a Malaria parasite in the sample, and wherein the absence of the amplification product is indicative of the absence of a Malaria parasite in the sample; and wherein the one or more set of primers and the one or more probes comprises: (1) a set of primers and a probe for the first target nucleic acid of a Malaria parasite, wherein the set of primers comprises a first primer comprising the nucleic acid sequence of SEQ ID NO:34, or a complement thereof, and a second primer comprising the nucleic acid sequence of SEQ ID NO:36, or a complement thereof; and wherein the probe comprises the nucleic acid sequence of SEQ ID NO:4, or a complement thereof; and/or (2) a set of primers and a probe for the second target nucleic acid of a Malaria parasite, wherein the set of primers comprises a first primer comprising the nucleic acid sequence of SEQ ID NO:22, or a complement thereof, and a second primer comprising the nucleic acid sequence of SEQ ID NO:27, or a complement thereof; and wherein the probe comprises the nucleic acid sequence of SEQ ID NO:25, or a complement thereof. Another aspect of the invention is directed to a method for detecting a Malaria parasite in a sample, the method comprising: (a) performing an amplification step comprising contacting the sample with one or more set of primers to produce an amplification product, if a target nucleic acid of a Malaria parasite is present in the sample; (b) performing a hybridization step comprising contacting the one or more probes with the amplification product, if the target nucleic acid of a Malaria parasite is present in the sample; and (c) detecting the presence or absence of the amplification product, wherein the presence of the amplification product is indicative of the presence of a Malaria parasite in the sample, and wherein the absence of the amplification product is indicative of the absence of a Malaria parasite in the sample; and wherein the one or more set of primers and the one or more probes comprises a set of primers comprising a first primer comprising the nucleic acid sequence of SEQ ID NO:34, or a complement thereof, and a second primer comprising the nucleic acid sequence of SEQ ID NO:36, or a complement thereof; and a probe comprising the nucleic acid sequence of SEQ ID NO:4, or a complement thereof. Another aspect is directed to a method for detecting a Malaria parasite in a sample, the method comprising: (a) performing an amplification step comprising contacting the sample with one or more set of primers to produce an amplification product, if a target nucleic acid of a Malaria parasite is present in the sample; (b) performing a hybridization step comprising contacting the one or more probes with the amplification product, if the target nucleic acid of a Malaria parasite is present in the sample; and (c) detecting the presence or absence of the amplification product, wherein the presence of the amplification product is indicative of the presence of a Malaria parasite in the sample, and wherein the absence of the amplification product is indicative of the absence of a Malaria parasite in the sample; and wherein the one or more set of primers and the one or more probes comprises a set of primers comprising a first primer comprising the nucleic acid sequence of SEQ ID NO:22, or a complement thereof, and a second primer comprising the nucleic acid sequence of SEQ ID NO:27, or a complement thereof; and a probe comprising the nucleic acid sequence of SEQ ID NO:25, or a complement thereof. In a related embodiment, the Malaria parasite belongs to the genus *Plasmodium*. In another embodiment, the Malaria parasite that belongs to the genus *Plasmodium* is *Plasmodium falciparum*. In another embodiment, the sample is a biological sample. In a related embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In one embodiment, the one or more probes is labeled. In another embodiment, the one or more probes is labeled with a donor fluorescent moiety and a corresponding acceptor moiety.

In one aspect, a kit for detecting a Malaria parasite that may be present in a sample is provided, the kit comprising amplification reagents comprising a DNA polymerase, nucleotide monomers (e.g., nucleoside triphosphates), and one or more set of primers and one or more probes, wherein the one or more set of primers and the one or more probes comprises: (1) a set of primers comprising a first primer comprising the nucleic acid sequence of SEQ ID NO:34, or a complement thereof, and a second primer comprising the nucleic acid sequence of SEQ ID NO:36, or a complement thereof; and a probe comprising the nucleic acid sequence of SEQ ID NO:4, or a complement thereof; and/or (2) a set of primers comprising a first primer comprising the nucleic acid sequence of SEQ ID NO:22, or a complement thereof, and a second primer comprising the nucleic acid sequence of SEQ ID NO:27, or a complement thereof; and a probe comprising the nucleic acid sequence of SEQ ID NO:25, or a complement thereof. In a related embodiment, the Malaria parasite belongs to the genus *Plasmodium*. In another embodiment, the Malaria parasite that belongs to the genus *Plasmodium* is *Plasmodium falciparum*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In another embodiment, the biological sample is whole blood. In one embodiment, the one or more probes is labeled. In another embodiment, the one or more probes is labeled with a donor fluorescent moiety and a corresponding acceptor moiety.

In one aspect, a kit for detecting a first target nucleic acid and/or a second target nucleic acid of a Malaria parasite that may be present in a sample is provided, the kit comprising amplification reagents comprising a DNA polymerase, nucleotide monomers (e.g., nucleoside triphosphates), and one or more set of primers and one or more probes, wherein the one or more set of primers and the one or more probes comprises: (1) a set of primers and a probe for the first target nucleic acid of a Malaria parasite, wherein the set of primers comprises a first primer comprising the nucleic acid sequence of SEQ ID NO:34, or a complement thereof, and a second primer comprising the nucleic acid sequence of SEQ ID NO:36, or a complement thereof; and wherein the probe comprising the nucleic acid sequence of SEQ ID NO:4, or a complement thereof; and/or (2) a set of primers and a probe for the second target nucleic acid of a Malaria parasite, wherein the set of primers comprises a first primer comprising the nucleic acid sequence of SEQ ID NO:22, or a complement thereof, and a second primer comprising the nucleic acid sequence of SEQ ID NO:27, or a complement thereof; and wherein the probe comprising the nucleic acid sequence of SEQ ID NO:25, or a complement thereof. Another aspect is directed to a kit for detecting a Malaria parasite that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: a first primer comprising the nucleic acid sequence of SEQ ID NO:34, or a complement thereof, and a second primer comprising the nucleic acid sequence of SEQ ID NO:36, or a complement thereof; and a probe comprising the nucleic acid sequence of SEQ ID NO:4, or a complement thereof. Another aspect is directed to a kit for detecting a Malaria parasite that may be present in a sample, the kit comprising amplification reagents comprising a DNA polymerase, nucleotide monomers (e.g., nucleoside triphosphates), and one or more set of primers and one or more probes, wherein the one or more set of primers and the one or more probes comprises: a first primer comprising the nucleic acid sequence of SEQ ID NO:22, or a complement thereof, and a second primer comprising the nucleic acid sequence of SEQ ID NO:27, or a complement thereof; and a probe comprising the nucleic acid sequence of SEQ ID NO:25, or a complement thereof. In a related embodiment, the Malaria parasite belongs to the genus *Plasmodium*. In another embodiment, the Malaria parasite that belongs to the genus *Plasmodium* is *Plasmodium falciparum*. In another embodiment, the sample is a biological sample. In another embodiment, the biological sample is whole blood, respiratory specimens, urine, fecal specimens, blood specimens, plasma, dermal swabs, nasal swabs, wound swabs, blood cultures, skin, or soft tissue infections. In one embodiment, the biological sample is whole blood. In another embodiment, the one or more probes is labeled. In another embodiment, the one or more probes is labeled with a donor fluorescent moiety and a corresponding acceptor moiety.

The disclosure in others aspects also provides an oligonucleotide comprising or consisting of a sequence of nucleotides selected from SEQ ID NOs:1-58, or a complement thereof, which oligonucleotide has 100 or fewer nucleotides. Herein, the present disclosure provides an oligonucleotide that includes a nucleic acid having at least 70% sequence identity (e.g., at least 75%, 80%, 85%, 90% or 95%, etc.) to one of SEQ ID NOs:1-58, or a complement thereof, which oligonucleotide has 100 or fewer nucleotides. Generally, these oligonucleotides may be primer nucleic acids, probe nucleic acids, or the like. In certain aspects, the oligonucleotides have 40 or fewer nucleotides (e.g., 35 or fewer nucleotides, 30 or fewer nucleotides, 25 or fewer nucleotides, 20 or fewer nucleotides, 15 or fewer nucleotides, etc.). In some aspects, the oligonucleotides comprise at least one modified nucleotide, e.g., to alter nucleic acid hybridization stability relative to unmodified nucleotides. Optionally, the oligonucleotides comprise at least one label and optionally at least one quencher moiety. In some aspects, the oligonucleotides include at least one conservatively modified variation. "Conservatively modified variations" or, simply, "conservative variations" of a particular nucleic acid sequence refers to those nucleic acids, which encode identical or essentially identical amino acid sequences, or, where the nucleic acid does not encode an amino acid sequence, to essentially identical sequences. One of skill in the art will recognize that individual substitutions, deletions or additions which alter, add or delete a single nucleotide or a small percentage of nucleotides (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid.

In one aspect, amplification can employ a polymerase enzyme having 5' to 3' nuclease activity. Thus, the donor fluorescent moiety and the acceptor moiety, e.g., a quencher, may be within no more than 5 to 20 nucleotides (e.g., within 7 or 10 nucleotides) of each other along the length of the probe. In another aspect, the oligonucleotide probe includes a nucleic acid sequence that permits secondary structure formation. Such secondary structure formation may result in spatial proximity between the first and second fluorescent moiety. According to this method, the second fluorescent moiety on the probe can be a quencher.

The present disclosure also provides for methods of detecting the presence or absence of Malaria parasites (such as *Plasmodium*) or Malaria parasites (such as *Plasmodium*) nucleic acid, in a biological sample from an individual. These methods can be employed to detect the presence or absence of Malaria parasites (such as *Plasmodium*) nucleic acid in plasma, for use in blood screening and diagnostic testing. Additionally, the same test may be used by someone experienced in the art to assess urine and other sample types to detect and/or quantitate Malaria parasites (such as *Plasmodium*) nucleic acid. Such methods generally include performing at least one cycling step, which includes an amplifying step and a dye-binding step. Typically, the amplifying step includes contacting the sample with a plurality of pairs of oligonucleotide primers to produce one or more amplification products if a nucleic acid molecule is present in the sample, and the dye-binding step includes contacting the amplification product with a double-stranded DNA binding dye. Such methods also include detecting the presence or absence of binding of the double-stranded DNA binding dye into the amplification product, wherein the presence of binding is indicative of the presence of Malaria parasites (such as *Plasmodium*) nucleic acid in the sample, and wherein the absence of binding is indicative of the absence of Malaria parasites nucleic acid in the sample. A representative double-stranded DNA binding dye is ethidium bromide. Other nucleic acid-binding dyes include DAPI, Hoechst dyes, PicoGreen®, RiboGreen®, OliGreen®, and cyanine dyes such as YO-YO® and SYBR® Green. In addition, such methods also can include determining the melting temperature between the amplification product and the double-stranded DNA binding dye, wherein the melting temperature confirms the presence or absence of Malaria parasite (including *Plasmodium*) nucleic acid.

In a further aspect, a kit for detecting and/or quantitating one or more nucleic acids of Malaria parasites (such as *Plasmodium*) is provided. The kit can include one or more sets of oligonucleotide primers specific for amplification of the gene target; and one or more detectable oligonucleotide probes specific for detection of the amplification products.

In one aspect, the kit can include probes already labeled with donor and corresponding acceptor moieties, e.g., another fluorescent moiety or a dark quencher, or can include fluorophoric moieties for labeling the probes. The kit can also include nucleoside triphosphates, nucleic acid polymerase, and buffers necessary for the function of the nucleic acid polymerase. The kit can also include a package insert and instructions for using the primers, probes, and fluorophoric moieties to detect the presence or absence of Malaria parasites (such as *Plasmodium*) nucleic acid in a sample.

Unless otherwise defined, all technical and scientific terms used herein have the same meaning as commonly understood by one of ordinary skill in the art to which this invention belongs. Although methods and materials similar or equivalent to those described herein can be used in the practice or testing of the present subject matter, suitable methods and materials are described below. In addition, the materials, methods, and examples are illustrative only and not intended to be limiting. All publications, patent applications, patents, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the drawings and detailed description, and from the claims.

BRIEF DESCRIPTION OF THE FIGURES

FIG. 2A shows data for the 18S-1 target (with primers having a nucleic acid sequence of SEQ ID NOs:1 and 2, and probe having a nucleic acid sequence of SEQ ID NO:3); FIG. 2B shows data for the 18S-3 target (with primers having a nucleic acid sequence of SEQ ID NOs:5 and 6, and probe having a nucleic acid sequence of SEQ ID NO:7); FIG. 2C shows data for the 18S-4 target (with primers having a nucleic acid sequence of SEQ ID NOs:8 and 9, and probe having a nucleic acid sequence of SEQ ID NO:10); FIG. 2D shows data for the MT-1 target (with primers having a nucleic acid sequence of SEQ ID NOs:16 and 17, and probe having a nucleic acid sequence of SEQ ID NO:18); FIG. 2E shows data for the MT-2 target (with primers having a nucleic acid sequence of SEQ ID NOs:11 and 12, and probe having a nucleic acid sequence of SEQ ID NO:15); and FIG. 2F shows data for the R125 target (with primers having a nucleic acid sequence of SEQ ID NOs:21 and 22, and probe having a nucleic acid sequence of SEQ ID NO:23).

FIG. 3 shows the data from Example 1 for eluates at the 1:$10^5$ dilution level.

FIG. 5 shows the ddPCR results of the *P. falciparum* culture. The results show the copy number (per μl) of 1:$10^5$ culture dilution of *P. falciparum* cultures. The studies for the 18S-1 target employed the primers having a nucleic acid sequence of SEQ ID NOs:1 and 2, and probe having a nucleic acid sequence of SEQ ID NO:37. The studies for the 18S-3 target employed the primers having a nucleic acid sequence of SEQ ID NOs:5 and 6, and probe having a nucleic acid sequence of SEQ ID NO:38. The studies for the 18S-4 target employed the primers having a nucleic acid sequence of SEQ ID NOs:8 and 9, and probe having a nucleic acid sequence of SEQ ID NO:39. The studies for the MT-1 target employed the primers having a nucleic acid sequence of SEQ ID NOs:16 and 17, and probe having a nucleic acid sequence of SEQ ID NO:42. The studies for the MT-2 target employed the primers having a nucleic acid sequence of SEQ ID NOs:11 and 12, and probe having a nucleic acid sequence of SEQ ID NO:41. The studies for the R125 target employed the primers having a nucleic acid sequence of SEQ ID NOs:21 and 22, and probe having a nucleic acid sequence of SEQ ID NO:40.

FIG. 6A shows the data from the multiplex assay with primers and probes for the 18S-1 and 18S-4 targets.

FIG. 7A shows the data from the multiplex assay with primers and probes for the 18S-1 and R125 targets, using *P. falciparum* from *P. falciparum* cultures at four different dilution levels (1:$10^4$, 1:$10^5$, 1:$10^6$, and 1:$10^7$), in a background of 500 ng of whole blood genomic DNA.

FIG. 8 shows the data from the multiplex assay with primers and probes for the 18S-1 and R125 targets, using in vitro transcripts of the 18S-1 and R125 targets at five different levels: $10^5$, $10^4$, $10^3$, $10^2$, and 10 copies), in a background of 500 ng of whole blood genomic DNA. For the 18S-1 target, this multiplex assay employed the primers having a nucleic acid sequence of SEQ ID NOs:1 and 2, and probe having a nucleic acid sequence of SEQ ID NO:4. For the R125 target, this multiplex assay employed the primers having a nucleic acid sequence of SEQ ID NOs:21 and 22, and probe having a nucleic acid sequence of SEQ ID NO:25.

FIG. 10A shows the data from the multiplex assay with primers and probes for the 18S-1 and R125 targets, using *P. falciparum* from *P. falciparum* cultures at four different dilution levels (1:$10^4$, 1:$10^5$, 1:$10^6$, and 1:$10^7$), in a background of whole blood nucleic acids that were extracted on the cobas 6800 instrument.

DETAILED DESCRIPTION OF THE INVENTION

Figure 1:
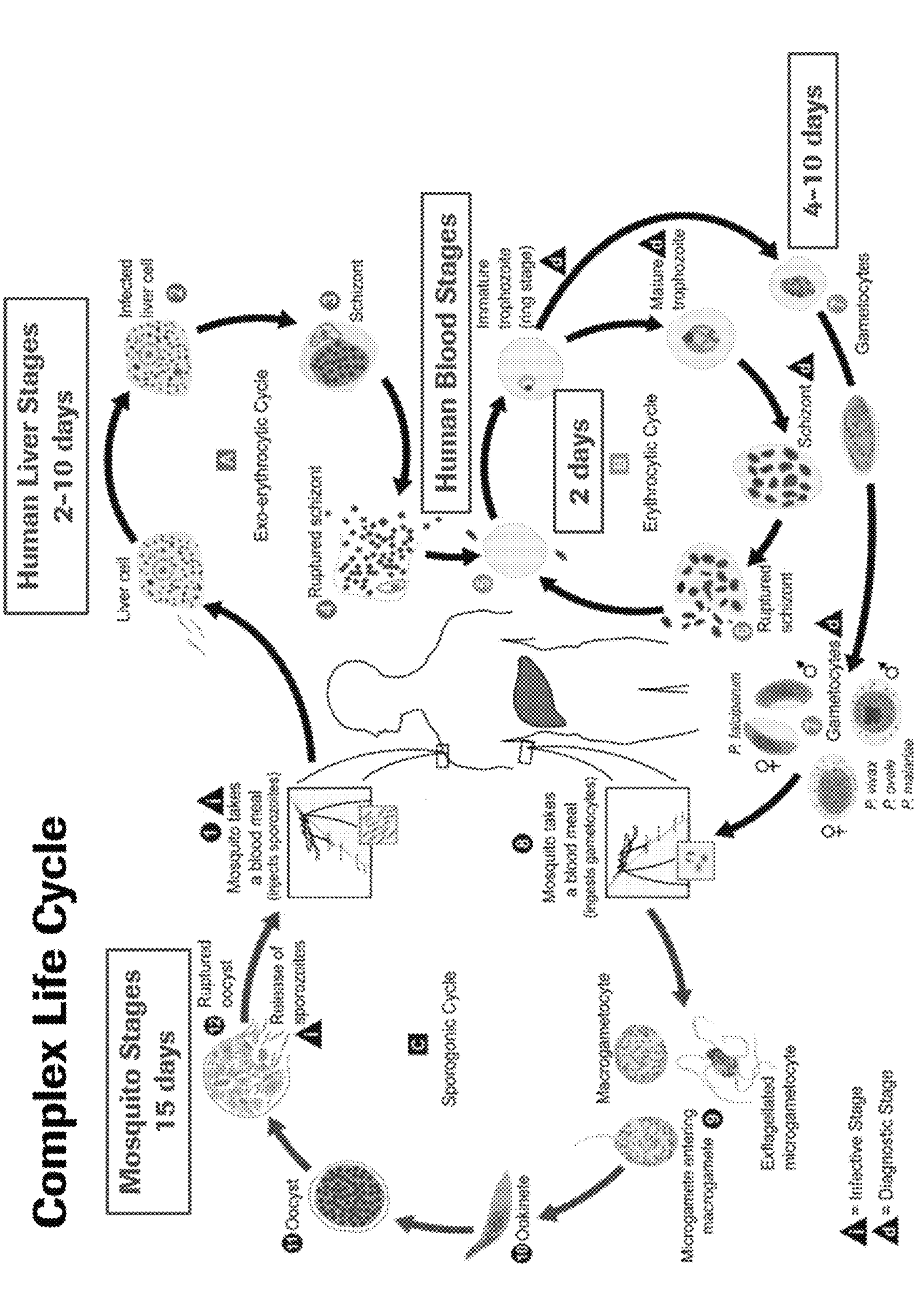
FIG. 1 depicts a diagram of the complex life cycle *Plasmodium*, with the parasite alternating between sexual reproduction in the mosquito and asexual reproduction in the human host (modified from the CDC website (https://www.cdc.gov/malaria)).

Diagnosis of Malaria parasites (such as *Plasmodium*) infection by nucleic acid amplification provides a method for rapidly, accurately, reliably, specifically, and sensitively detecting and/or quantitating the Malaria parasites (such as *Plasmodium*) infection. A real-time PCR assay for detecting and/or quantitating Malaria parasites nucleic acids, including DNA and/or RNA, in a non-biological or biological sample is described herein. Primers and probes for detecting and/or quantitating Malaria parasites (such as *Plasmodium*) are provided, as are articles of manufacture or kits containing such primers and probes. The increased specificity and sensitivity of real-time PCR for detection of Malaria parasites (such as *Plasmodium*) compared to other methods, as well as the improved features of real-time PCR including sample containment and real-time detection and quantitating of the amplified product, make feasible the implementation of this technology for routine diagnosis of Malaria parasites (such as *Plasmodium*) infections in the clinical laboratory. Additionally, this technology may be employed for blood screening as well as for prognosis. This Malaria parasites (such as *Plasmodium*) detection assay may also be multiplexed with other assays for the detection of other nucleic acids, e.g., other bacteria and/or viruses, in parallel.

The present disclosure includes oligonucleotide primers and fluorescent labeled hydrolysis probes that hybridize to the Malaria parasites (such as *Plasmodium*) genome, in order to specifically identify Malaria parasites (such as *Plasmodium*) using, e.g., TaqMan® amplification and detection technology.

The disclosed methods may include performing at least one cycling step that includes amplifying one or more portions of the nucleic acid molecule gene target from a sample using one or more pairs of primers. "*Plasmodium* primer(s)" as used herein refer to oligonucleotide primers that specifically anneal to nucleic acid sequences found in the Malaria parasites (such as *Plasmodium*) genome, and initiate DNA synthesis therefrom under appropriate conditions producing the respective amplification products. Examples of nucleic acid sequences found in the *Plasmodium* species and genome include targets such as nucleic acids within the Mitochondrial DNA target area (MT-1 and MT-2), RNA repeat sequences R125, and 18S Ribosomal RNA. Each of the discussed *Plasmodium* primers anneals to a target such that at least a portion of each amplification product contains nucleic acid sequence corresponding to the target. The one or more amplification products are produced provided that one or more nucleic acid is present in the sample, thus the presence of the one or more amplification products is indicative of the presence of *Plasmodium* in the sample. The amplification product should contain the nucleic acid sequences that are complementary to one or more detectable probes for *Plasmodium*. "*Plasmodium* probe(s)" as used herein refer to oligonucleotide probes that specifically anneal to nucleic acid sequences found in the *Plasmodium* genome. Each cycling step includes an amplification step, a hybridization step, and a detection step, in which the sample is contacted with the one or more detectable *Plasmodium* probes for detection of the presence or absence of *Plasmodium* in the sample.

As used herein, the term "amplifying" refers to the process of synthesizing nucleic acid molecules that are complementary to one or both strands of a template nucleic acid molecule (e.g., nucleic acid molecules from the *Plasmodium* genome). Amplifying a nucleic acid molecule typically includes denaturing the template nucleic acid, annealing primers to the template nucleic acid at a temperature that is below the melting temperatures of the primers, and enzymatically elongating from the primers to generate an amplification product. Amplification typically requires the presence of deoxyribonucleoside triphosphates, a DNA polymerase enzyme (e.g., Platinum® Taq) and an appropriate buffer and/or co-factors for optimal activity of the polymerase enzyme (e.g., $MgCl_2$ and/or KCl).

The term "primer" as used herein is known to those skilled in the art and refers to oligomeric compounds, primarily to oligonucleotides but also to modified oligonucleotides that are able to "prime" DNA synthesis by a template-dependent DNA polymerase, i.e., the 3'-end of the, e.g., oligonucleotide provides a free 3'-OH group where further "nucleotides" may be attached by a template-dependent DNA polymerase establishing 3' to 5' phosphodiester linkage whereby deoxynucleoside triphosphates are used and whereby pyrophosphate is released.

The term "hybridizing" refers to the annealing of one or more probes to an amplification product. "Hybridization conditions" typically include a temperature that is below the melting temperature of the probes but that avoids non-specific hybridization of the probes.

The term "5' to 3' nuclease activity" refers to an activity of a nucleic acid polymerase, typically associated with the nucleic acid strand synthesis, whereby nucleotides are removed from the 5' end of nucleic acid strand.

The term "thermostable polymerase" refers to a polymerase enzyme that is heat stable, i.e., the enzyme catalyzes the formation of primer extension products complementary to a template and does not irreversibly denature when subjected to the elevated temperatures for the time necessary to effect denaturation of double-stranded template nucleic acids. Generally, the synthesis is initiated at the 3' end of each primer and proceeds in the 5' to 3' direction along the template strand. Thermostable polymerases have been isolated from *Thermus flavus, T. ruber, T. thermophilus, T. aquaticus, T. lacteus, T. rubens, Bacillus stearothermophilus*, and *Methanothermus fervidus*. Nonetheless, polymerases that are not thermostable also can be employed in PCR assays provided the enzyme is replenished, if necessary.

The term "complement thereof" refers to nucleic acid that is both the same length as, and exactly complementary to, a given nucleic acid.

The term "extension" or "elongation" when used with respect to nucleic acids refers to when additional nucleotides (or other analogous molecules) are incorporated into the nucleic acids. For example, a nucleic acid is optionally extended by a nucleotide incorporating biocatalyst, such as a polymerase that typically adds nucleotides at the 3' terminal end of a nucleic acid.

The terms "identical" or percent "identity" in the context of two or more nucleic acid sequences, refer to two or more sequences or subsequences that are the same or have a specified percentage of nucleotides that are the same, when compared and aligned for maximum correspondence, e.g., as measured using one of the sequence comparison algorithms available to persons of skill or by visual inspection. Exemplary algorithms that are suitable for determining percent sequence identity and sequence similarity are the BLAST programs, which are described in, e.g., Altschul et al. (1990) "Basic local alignment search tool" *J. Mol. Biol.* 215:403-410, Gish et al. (1993) "Identification of protein coding regions by database similarity search" *Nature Genet.* 3:266-272, Madden et al. (1996) "Applications of network BLAST server" *Meth. Enzymol.* 266:131-141, Altschul et al. (1997) "Gapped BLAST and PSI-BLAST: a new generation of protein database search programs" *Nucleic Acids Res.* 25:3389-3402, and Zhang et al. (1997) "PowerBLAST: A new network BLAST application for interactive or automated sequence analysis and annotation" *Genome Res.* 7:649-656, which are each incorporated herein by reference.

A "modified nucleotide" in the context of an oligonucleotide refers to an alteration in which at least one nucleotide of the oligonucleotide sequence is replaced by a different nucleotide that provides a desired property to the oligonucleotide. Exemplary modified nucleotides that can be substituted in the oligonucleotides described herein include, e.g., a t-butyl benzyl, a C5-methyl-dC, a C5-ethyl-dC, a C5-methyl-dU, a C5-ethyl-dU, a 2,6-diaminopurine, a C5-propynyl-dC, a C5-propynyl-dU, a C7-propynyl-dA, a C7-propynyl-dG, a C5-propargylamino-dC, a C5-propargylamino-dU, a C7-propargylamino-dA, a C7-propargylamino-dG, a 7-deaza-2-deoxyxanthosine, a pyrazolopyrimidine analog, a pseudo-dU, a nitro pyrrole, a nitro indole, 2'-0-methyl ribo-U, 2'-0-methyl ribo-C, an N4-ethyl-dC, an N6-methyl-dA, a 5-propynyl dU, a 5-propynyl dC, 7-deaza-deoxyguanosine (deaza G (u-deaza)) and the like. Many other modified nucleotides that can be substituted in the oligonucleotides are referred to herein or are otherwise known in the art. In certain embodiments, modified nucleotide substitutions modify melting temperatures (Tm) of the oligonucleotides relative to the melting temperatures of corresponding unmodified oligonucleotides. To further illustrate, certain modified nucleotide substitutions can reduce non-specific nucleic acid amplification (e.g., minimize primer dimer formation or the like), increase the yield of an intended target amplicon, and/or the like in some embodiments. Examples of these types of nucleic acid modifications are described in, e.g., U.S. Pat. No. 6,001,611, which is incorporated herein by reference. Other modified nucleotide substitutions may alter the stability of the oligonucleotide, or provide other desirable features.

Detection/Quantitation of Malaria Parasite (Including *Plasmodium*) Target Nucleic Acid The present disclosure provides methods to detect Malaria parasites (including *Plasmodium*) by amplifying, for example, a portion of the *Plasmodium* nucleic acid sequence. Specifically, primers and probes to amplify and detect and/or quantitate *Plasmodium* nucleic acid molecule targets are provided by the embodiments in the present disclosure.

For detection and/or quantitation of Malaria parasites (including *Plasmodium*), primers and probes to amplify and detect/quantitate the *Plasmodium* are provided. *Plasmodium* nucleic acids other than those exemplified herein can also be used to detect *Plasmodium* in a sample. For example, functional variants can be evaluated for specificity and/or sensitivity by those of skill in the art using routine methods. Representative functional variants can include, e.g., one or more deletions, insertions, and/or substitutions in the *Plasmodium* nucleic acids disclosed herein.

More specifically, embodiments of the oligonucleotides each include a nucleic acid with a sequence selected from SEQ ID NOs:1-58, a substantially identical variant thereof in which the variant has at least, e.g., 80%, 90%, or 95% sequence identity to one of SEQ ID NOs:1-58, or a complement of SEQ ID NOs:1-58 and the variant.

TABLE 1

Oligonucleotides (primers and probes) used in *Plasmodium* assay

| Type | Oligo ID & SEQ ID NO: | Sequence |
|---|---|---|
| F. Primer | PM-18S_1F (SEQ ID NO: 1) | GGAGCCTGAGAAATAGCTACCA<t_BB_dC> |
| R. Primer | PM-18S_1R (SEQ ID NO: 2) | TTTCTTGTCACTACCTCTCTTCTTTAGA<t_BB_dA> |
| Probe | PM-18S_1P (SEQ ID NO: 3) | <FAM_Thr>AAGGA<BHQ_2>AGGCAGCAGGCGCGTAAATTACCC<Spc_C3> |
| Probe | PM-18S_1P2 (SEQ ID NO: 4) | <FAM_Thr>AGGCA<BHQ_2>GCAGGCGCGTAAATTACCCAA<Spc_C3> |
| F. Primer | PM-18S 2A1F (SEQ ID NO: 5) | CGGAAGGGCACCACC<t_BB_dA> |
| R. Primer | PM-18S 2AIR (SEQ ID NO: 6) | ATCTGTCAATCCTACTCTTGTCTTAAACT<t_BB_dA> |
| Probe | PM-18S 2A1P (SEQ ID NO: 7) | <FAM_Thr>TGGAG<BHQ_2>CTTGCGGCTTAATTTGACTCAACACGG<Spc_C3> |
| F. Primer | PM-18S 2A2F (SEQ ID NO: 8) | ACAAGAGTAGGATTGACAGATTAATAGCT<t_BB_dC> |
| R. Primer | PM-18S_2A2R (SEQ ID NO: 9) | CGTTATCGGAATTAACCAGACAAATCAT<t_BB_dA> |
| Probe | PM-18S_2A2P (SEQ ID NO: 10) | <FAM_Thr>TGGAT<BHQ_2>GGTGATGCATGGCCGTTTTTAGTTCGT<Spc_C3> |
| F. Primer | RM_44F1 (SEQ ID NO: 11) | ACAGGTTAACGCCTGGAGTT<t_BB_dC> |
| R. Primer | RM_44R1 (SEQ ID NO: 12) | TGTCGTCTCATCGCAGC<t_BB_dC> |
| R. Primer | RM_44R2.MOD (SEQ ID NO: 13) | GCACCTCCATGTCGTCTC<t_BB_dA> |
| R. Primer | RM_44R3.MOD (SEQ ID NO: 14) | TCTTTATATACTATTGGCACCTCCATGT<t_BB_dC> |
| Probe | RM_44P1 (SEQ ID NO: 15) | <HEX Thr>CGTGAC<BHQ_2>GAGCGGTGTGTACAAGGCAACA<Phos> |

TABLE 1-continued

Oligonucleotides (primers and probes) used in *Plasmodium* assay

| Type | Oligo ID & SEQ ID NO: | Sequence |
|---|---|---|
| F. Primer | RM_75F1 (SEQ ID NO: 16) | TCTGCCCGGCATCAATGATAA<t_BB_dA> |
| R. Primer | RM_75R1 (SEQ ID NO: 17) | GGAGTCTCACACTAGCGACA<t_BB_dA> |
| Probe | RM_75P1 (SEQ ID NO: 18) | <HEX Thr>CCTTGTCG<BHQ_2>GGTAATCTCCGTCCTGCATGAACG<Phos> |
| Probe | RM_75P1_FAM (SEQ ID NO: 19) | <FAM_Thr>CCTTGTCG<BHQ_2>GGTAATCTCCGTCCTGCATGAACG<Spc_C3> |
| Probe | RM_75P1_FAMQ5 (SEQ ID NO: 20) | <FAM_Thr>CCTTG<BHQ_2>TCGGGTAATCTCCGTCCTGCATGAACG<Spc_C3> |
| F. Primer | RM_125F1 (SEQ ID NO: 21) | TTCTGCGTCCCAATGATAGGA<t_BB_dA> |
| R. Primer | RM_125R1 (SEQ ID NO: 22) | GGCCTATCGATCCTTTATATTTGC<t_BB_dA> |
| Probe | RM_125P1 (SEQ ID NO: 23) | <HEX Thr>ACGTCG<BHQ_2>CTAGGAGCGCTTGGCAGC<Phos> |
| Probe | RM_125P1_FAM (SEQ ID NO: 24) | <FAM_Thr>ACGTCG<BHQ_2>CTAGGAGCGCTTGGCAGC<Spc_C3> |
| Probe | RM_125P1_FAMQ5 (SEQ ID NO: 25) | <FAM_Thr>ACGTC<BHQ_2>GCTAGGAGCGCTTGGCAGC<Spc_C3> |
| F. Primer | RM125_F44 (SEQ ID NO: 26) | TGAACAATCCGACACTTTGAGAC |
| F. Primer | R125_F44_TBBC (SEQ ID NO: 27) | TGAACAATCCGACACTTTGAGA<t_BB_dC> |
| F. Primer | R125B_FOR2 (SEQ ID NO: 28) | GCCACGCTTTCACGTTTTC |
| R. Primer | R125B_REV1 (SEQ ID NO: 29) | CGGTACATCTGTTAAAAAATAACGCA |
| Probe | R125B_PIMOD2 (SEQ ID NO: 30) | <FAM_Thr>AGA<pdU><pdU><BHQ_2><pdU><pdC>TGTTCTCTTTGAGCT TGTCTTTGGACAT<Spc_C3> |
| F. Primer | 18S-1_F332 (SEQ ID NO: 31) | GGGTATTGGCCTAACATGGCTA |
| F. Primer | 18S-1_F332_INC (SEQ ID NO: 32) | GGGTATTGACCTAACATGGCTA |
| R. Primer | PM-18S_1R_2 (SEQ ID NO: 33) | TTTCTTGTCACTACCTCTCTTCTTTAGA |
| F. Primer | 18S-1_F333_TBBA (SEQ ID NO: 34) | GGTATTGGCCTAACATGGCTATG<t_BB_dA> |
| F. Primer | 18S-1_F333_INC (SEQ ID NO: 35) | GGTATTGACCTAACATGGCTATG<t_BB_dA> |
| R. Primer | PM-18S_1RM2 (SEQ ID NO: 36) | TTTCTTGTCACTACCTCTCTTCTTTAG<t_BB_dA>A |
| Probe | DDPM-18S_1P (SEQ ID NOS 44 and 45, respectively; full-length sequence disclosed as SEQ ID NO: 37) | <FAM_Thr>AAGGAAGGCA<ZEN>GCAGGCGCGTAAATTACCC<IB_FQ> |

TABLE 1-continued

Oligonucleotides (primers and probes) used in *Plasmodium* assay

| Type | Oligo ID & SEQ ID NO: | Sequence |
|---|---|---|
| Probe | DDPM-18S_2A1P (SEQ ID NOS 46 and 47, respectively; full-length sequence disclosed as SEQ ID NO: 38) | <FAM_Thr>TGGAGCTTGC<ZEN>GGCTTAATTTGACTCAACACGG<IB_FQ> |
| Probe | DDPM-18S_2A2P (SEQ ID NOS 48 and 49, respectively; full-length sequence disclosed as SEQ ID NO: 39) | <FAM_Thr>TGGATGGTGA<ZEN>TGCATGGCCGTTTTTAGTTCGT<IB_FQ> |
| Probe | DDRM_125P1 (SEQ ID NOS 50 and 51, respectively; full-length sequence disclosed as SEQ ID NO: 40) | <FAM_Thr>ACGTCGCTAG<ZEN>GAGCGCTTGGCAGC<IB_FQ> |
| Probe | DD_RM_44P1 (SEQ ID NOS 52 and 53, respectively; full-length sequence disclosed as SEQ ID NO: 41) | <FAM_Thr>CGTGACGAG<ZEN>CGGTGTGTACAAGGCAACA<IB_FQ> |
| Probe | DDRM_75P1 (SEQ ID NOS 54 and 55, respectively; full-length sequence disclosed as SEQ ID NO: 42) | <FAM_Thr>CCTTGTCGGG<ZEN>TAATCTCCGTCCTGCATGAACG<IB_FQ> |
| R. Primer | RM_125R1_2INC (SEQ ID NO: 43) | GGCCTATCGATATCCTTTATGTTTG<t_BB_dC> |
| F. Primer | 18S_1273F2_TBBA (SEQ ID NO: 56) | CAACACGGGAAAACTCACTAGTTT<t_BB_dA> |
| R. Primer | 18S_1273R1 (SEQ ID NO: 57) | ACCAGACAAATCATATTCACGAACTAAA |
| Probe | 18S_1273P1MOD (SEQ ID NO: 58) | <FAM_Thr>TGA<pdU><pdU><BHQ_2>TCTTGGATGGTGATGCATGGCC GT<Spc_C3> |

In one embodiment, the above described sets of *Plasmodium* primers and probes are used in order to provide for detection of Malaria parasites (including *Plasmodium*) in a biological sample suspected of containing *Plasmodium* (Table 1). The sets of primers and probes may comprise or consist of the primers and probes specific for the nucleic acid sequences of Malaria parasites (including *Plasmodium*), comprising or consisting of the nucleic acid sequences of SEQ ID NOs:1-58. In another embodiment, the primers and probes for the *Plasmodium* target comprise or consist of a functionally active variant of any of the primers and probes of SEQ ID NOs:1-58.

A functionally active variant of any of the primers and/or probes of SEQ ID NOs:1-58 may be identified by using the primers and/or probes in the disclosed methods. A functionally active variant of a primer and/or probe of any of the SEQ ID NOs:1-58 pertains to a primer and/or probe which provide a similar or higher specificity and sensitivity in the described method or kit as compared to the respective sequence of SEQ ID NOs:1-58.

The variant may, e.g., vary from the sequence of SEQ ID NOs:1-58 by one or more nucleotide additions, deletions or substitutions such as one or more nucleotide additions, deletions or substitutions at the 5' end and/or the 3' end of the respective sequence of SEQ ID NOs:1-58. As detailed above, a primer and/or probe may be chemically modified, i.e., a primer and/or probe may comprise a modified nucleotide or a non-nucleotide compound. A probe (or a primer) is then a modified oligonucleotide. "Modified nucleotides" (or "nucleotide analogs") differ from a natural "nucleotide" by some modification but still consist of a base or base-like compound, a pentofuranosyl sugar or a pentofuranosyl sugar-like compound, a phosphate portion or phosphate-like portion, or combinations thereof. For example, a "label" may be attached to the base portion of a "nucleotide" whereby a "modified nucleotide" is obtained. A natural base in a "nucleotide" may also be replaced by, e.g., a 7-desazapurine whereby a "modified nucleotide" is obtained as well. The terms "modified nucleotide" or "nucleotide analog" are used interchangeably in the present application. A "modified nucleoside" (or "nucleoside analog") differs from a natural nucleoside by some modification in the manner as outlined above for a "modified nucleotide" (or a "nucleotide analog").

Oligonucleotides including modified oligonucleotides and oligonucleotide analogs that amplify a nucleic acid molecule encoding the *Plasmodium* target, e.g., nucleic acids encoding alternative portions of *Plasmodium* can be designed using, for example, a computer program such as OLIGO (Molecular Biology Insights Inc., Cascade, Colo.). Important features when designing oligonucleotides to be used as amplification primers include, but are not limited to, an appropriate size amplification product to facilitate detection (e.g., by electrophoresis), similar melting temperatures for the members of a pair of primers, and the length of each primer (i.e., the primers need to be long enough to anneal with sequence-specificity and to initiate synthesis but not so long that fidelity is reduced during oligonucleotide synthesis). Typically, oligonucleotide primers are 8 to 50 nucleotides in length (e.g., 8, 10, 12, 14, 16, 18, 20, 22, 24, 26, 28, 30, 32, 34, 36, 38, 40, 42, 44, 46, 48, or 50 nucleotides in length). The disclosed primers for detection and amplification of Malaria parasites (including *Plasmodium*) include SEQ ID NOs: 1, 2, 5, 6, 8, 9, 11-14, 16, 17, 21, 22, 26-29, 31-36, 43, 56, and 57.

In addition to a set of primers, the methods may use one or more probes in order to detect the presence or absence of *Plasmodium*. The term "probe" refers to synthetically or biologically produced nucleic acids (DNA or RNA), which by design or selection, contain specific nucleotide sequences that allow them to hybridize under defined predetermined stringencies specifically (i.e., preferentially) to "target nucleic acids", in the present case to a *Plasmodium* (target) nucleic acid. A "probe" can be referred to as a "detection probe" meaning that it detects the target nucleic acid. In some embodiments, the described *Plasmodium* probes can be labeled with at least one fluorescent label. In one embodiment, the *Plasmodium* probes can be labeled with a donor fluorescent moiety, e.g., a fluorescent dye, and a corresponding acceptor moiety, e.g., a quencher. In one embodiment, the probe comprises or consists of a fluorescent moiety and the nucleic acid sequences comprise or consist of SEQ ID NOs:3, 4, 7, 10, 15, 18-20, 23-25, 30, 37-42, and 58. The disclosed probes for detection of Malaria parasites (including *Plasmodium*), via, for example, hybridization/annealing to amplicons, include SEQ ID NOs: 3, 4, 7, 10, 15, 18-20, 23-25, 30, 37-42, and 58.

Designing oligonucleotides to be used as probes can be performed in a manner similar to the design of primers. Embodiments may use a single probe or a pair of probes for detection of the amplification product. Depending on the embodiment, the probe(s) use may comprise at least one label and/or at least one quencher moiety. As with the primers, the probes usually have similar melting temperatures, and the length of each probe must be sufficient for sequence-specific hybridization to occur but not so long that fidelity is reduced during synthesis. Oligonucleotide probes are generally 15 to 40 (e.g., 15, 16, 18, 20, 21, 22, 23, 24, 25, 26, 27, 28, 29, 30, 31, 32, 33, 34, 35, 36, 37, 39, or 40) nucleotides in length.

Constructs can include vectors each containing one of *Plasmodium* primers and probes nucleic acid molecules (e.g., SEQ ID NOs:1-58). Constructs can be used, for example, as control template nucleic acid molecules. Vectors suitable for use are commercially available and/or produced by recombinant nucleic acid technology methods routine in the art. *Plasmodium* nucleic acid molecules can be obtained, for example, by chemical synthesis, direct cloning from *Plasmodium*, or by nucleic acid amplification.

Constructs suitable for use in the methods typically include, in addition to the *Plasmodium* nucleic acid molecules, and/or primers/probes for amplification and/or detection of *Plasmodium* (e.g., a nucleic acid molecule that contains one or more sequences of SEQ ID NOs:1-58), sequences encoding a selectable marker (e.g., an antibiotic resistance gene) for selecting desired constructs and/or transformants, and an origin of replication. The choice of vector systems usually depends upon several factors, including, but not limited to, the choice of host cells, replication efficiency, selectability, inducibility, and the ease of recovery.

Constructs containing *Plasmodium* nucleic acid molecules, and/or primers/probes for amplification and/or detection of *Plasmodium*, can be propagated in a host cell. As used herein, the term host cell is meant to include prokaryotes and eukaryotes such as yeast, plant and animal cells. Prokaryotic hosts may include *E. coli, Salmonella typhimurium, Serratia marcescens*, and *Bacillus subtilis*. Eukaryotic hosts include yeasts such as *S. cerevisiae, S. pombe, Pichia pastoris*, mammalian cells such as COS cells or Chinese hamster ovary (CHO) cells, insect cells, and plant cells such as *Arabidopsis thaliana* and *Nicotiana tabacum*. A construct can be introduced into a host cell using any of the techniques commonly known to those of ordinary skill in the art. For example, calcium phosphate precipitation, electroporation, heat shock, lipofection, microinjection, and viral-mediated nucleic acid transfer are common methods for introducing nucleic acids into host cells. In addition, naked DNA can be delivered directly to cells (see, e.g., U.S. Pat. Nos. 5,580,859 and 5,589,466).

Polymerase Chain Reaction (PCR)

U.S. Pat. Nos. 4,683,202, 4,683,195, 4,800,159, and 4,965,188 disclose conventional PCR techniques. PCR typically employs two oligonucleotide primers that bind to a selected nucleic acid template (e.g., DNA or RNA). Primers useful in some embodiments include oligonucleotides capable of acting as points of initiation of nucleic acid synthesis within the described *Plasmodium* nucleic acid sequences (e.g., SEQ ID NOs: 1, 2, 5, 6, 8, 9, 11-14, 16, 17, 21, 22, 26-29, 31-36, and 43). A primer can be purified from a restriction digest by conventional methods, or it can be produced synthetically. The primer is preferably single-stranded for maximum efficiency in amplification, but the primer can be double-stranded. Double-stranded primers are first denatured, i.e., treated to separate the strands. One method of denaturing double stranded nucleic acids is by heating.

If the template nucleic acid is double-stranded, it is necessary to separate the two strands before it can be used as a template in PCR. Strand separation can be accomplished by any suitable denaturing method including physical, chemical or enzymatic means. One method of separating the nucleic acid strands involves heating the nucleic acid until it is predominately denatured (e.g., greater than 50%, 60%, 70%, 80%, 90% or 95% denatured). The heating conditions necessary for denaturing template nucleic acid will depend, e.g., on the buffer salt concentration and the length and nucleotide composition of the nucleic acids being denatured, but typically range from about 90° C. to about 105° C. for a time depending on features of the reaction such as temperature and the nucleic acid length. Denaturation is typically performed for about 30 sec to 4 min (e.g., 1 min to 2 min 30 sec, or 1.5 min).

If the double-stranded template nucleic acid is denatured by heat, the reaction mixture is allowed to cool to a temperature that promotes annealing of each primer to its target sequence. The temperature for annealing is usually from about 35° C. to about 65° C. (e.g., about 40° C. to about 60° C.; about 45° C. to about 50° C.). Annealing times can be from about 10 sec to about 1 min (e.g., about 20 sec to about 50 sec; about 30 sec to about 40 sec). The reaction mixture is then adjusted to a temperature at which the activity of the polymerase is promoted or optimized, i.e., a temperature sufficient for extension to occur from the annealed primer to generate products complementary to the template nucleic acid. The temperature should be sufficient to synthesize an extension product from each primer that is annealed to a nucleic acid template, but should not be so high as to denature an extension product from its complementary template (e.g., the temperature for extension generally ranges from about 40° C. to about 80° C. (e.g., about 50° C. to about 70° C.; about 60° C.). Extension times can be from about 10 sec to about 5 min (e.g., about 30 sec to about 4 min; about 1 min to about 3 min; about 1 min 30 sec to about 2 min).

The genome of a retrovirus or RNA virus is comprised of a ribonucleic acid, i.e., RNA. In such case, the template nucleic acid, RNA, must first be transcribed into complementary DNA (cDNA) via the action of the enzyme reverse transcriptase. Reverse transcriptases use an RNA template and a short primer complementary to the 3' end of the RNA to direct synthesis of the first strand cDNA, which can then be used directly as a template for polymerase chain reaction.

PCR assays can employ *Plasmodium* nucleic acid, and/or primers/probes that amplify and/or detect *Plasmodium*, such as RNA or DNA (cDNA). The template nucleic acid need not be purified; it may be a minor fraction of a complex mixture, such as *Plasmodium* nucleic acid contained in human cells. *Plasmodium* nucleic acid molecules, and/or primers/probes that amplify and/or detect *Plasmodium* may be extracted from a biological sample by routine techniques such as those described in *Diagnostic Molecular Microbiology: Principles and Applications* (Persing, et al. (eds), 1993, American Society for Microbiology, Washington D.C.). Nucleic acids can be obtained from any number of sources, such as plasmids, or natural sources including bacteria, yeast, viruses, organelles, or higher organisms such as plants or animals.

The oligonucleotide primers (e.g., SEQ ID NOs:1, 2, 5, 6, 8, 9, 11-14, 16, 17, 21, 22, 26-29, 31-36, and 43) are combined with PCR reagents under reaction conditions that induce primer extension. For example, chain extension reactions generally include 50 mM KCl, 10 mM Tris-HCl (pH 8.3), 15 mM $MgCl_2$, 0.001% (w/v) gelatin, 0.5-1.0 μg denatured template DNA, 50 pmoles of each oligonucleotide primer, 2.5 U of Taq polymerase, and 10% DMSO). The reactions usually contain 150 to 320 μM each of dATP, dCTP, dTTP, dGTP, or one or more analogs thereof.

The newly-synthesized strands form a double-stranded molecule that can be used in the succeeding steps of the reaction. The steps of strand separation, annealing, and elongation can be repeated as often as needed to produce the desired quantity of amplification products corresponding to the target nucleic acid molecules of Malaria parasites (including *Plasmodium*). The limiting factors in the reaction are the amounts of primers, thermostable enzyme, and nucleoside triphosphates present in the reaction. The cycling steps (i.e., denaturation, annealing, and extension) are preferably repeated at least once. For use in detection, the number of cycling steps will depend, e.g., on the nature of the sample. If the sample is a complex mixture of nucleic acids, more cycling steps will be required to amplify the target sequence sufficient for detection. Generally, the cycling steps are repeated at least about 20 times, but may be repeated as many as 40, 60, or even 100 times.

Fluorescence Resonance Energy Transfer (FRET)

FRET technology (see, for example, U.S. Pat. Nos. 4,996,143, 5,565,322, 5,849,489, and 6,162,603) is based on a concept that when a donor fluorescent moiety and a corresponding acceptor fluorescent moiety are positioned within a certain distance of each other, energy transfer takes place between the two fluorescent moieties that can be visualized or otherwise detected and/or quantitated. The donor typically transfers the energy to the acceptor when the donor is excited by light radiation with a suitable wavelength. The acceptor typically re-emits the transferred energy in the form of light radiation with a different wavelength. In certain systems, non-fluorescent energy can be transferred between donor and acceptor moieties, by way of biomolecules that include substantially non-fluorescent donor moieties (see, for example, U.S. Pat. No. 7,741,467).

In one example, an oligonucleotide probe can contain a donor fluorescent moiety or dye (e.g., HEX or FAM) and a corresponding quencher (e.g., BlackHole Quencher™ (BHQ) (such as BHQ-2)), which may or not be fluorescent, and which dissipates the transferred energy in a form other than light. When the probe is intact, energy transfer typically occurs between the donor and acceptor moieties such that fluorescent emission from the donor fluorescent moiety is quenched the acceptor moiety. During an extension step of a polymerase chain reaction, a probe bound to an amplification product is cleaved by the 5' to 3' nuclease activity of, e.g., a Taq Polymerase such that the fluorescent emission of the donor fluorescent moiety is no longer quenched. Exemplary probes for this purpose are described in, e.g., U.S. Pat. Nos. 5,210,015, 5,994,056, and 6,171,785. Commonly used donor-acceptor pairs include the FAM-TAMRA pair. Commonly used quenchers are DABCYL and TAMRA. Commonly used dark quenchers include BlackHole Quencher™ (BHQ) (such as BHQ2), (Biosearch Technologies, Inc., Novato, Cal.), Iowa Black™, (Integrated DNA Tech., Inc., Coralville, Iowa), BlackBerry™ Quencher 650 (BBQ-650), (Berry & Assoc., Dexter, Mich.).

In another example, two oligonucleotide probes, each containing a fluorescent moiety, can hybridize to an amplification product at particular positions determined by the complementarity of the oligonucleotide probes to the *Plasmodium* target nucleic acid sequence. Upon hybridization of the oligonucleotide probes to the amplification product nucleic acid at the appropriate positions, a FRET signal is generated. Hybridization temperatures can range from about 35° C. to about 65° C. for about 10 sec to about 1 min.

Fluorescent analysis can be carried out using, for example, a photon counting epifluorescent microscope system (containing the appropriate dichroic mirror and filters for monitoring fluorescent emission at the particular range), a photon counting photomultiplier system, or a fluorimeter. Excitation to initiate energy transfer, or to allow direct detection of a fluorophore, can be carried out with an argon ion laser, a high intensity mercury (Hg) arc lamp, a xenon lamp, a fiber optic light source, or other high intensity light source appropriately filtered for excitation in the desired range. As used herein with respect to donor and corresponding acceptor moieties "corresponding" refers to an acceptor fluorescent moiety or a dark quencher having an absorbance spectrum that overlaps the emission spectrum of the donor fluorescent moiety. The wavelength maximum of the emission spectrum of the acceptor fluorescent moiety should be at least 100 nm greater than the wavelength maximum of the excitation spectrum of the donor fluorescent moiety. Accordingly, efficient non-radiative energy transfer can be produced therebetween.

Fluorescent donor and corresponding acceptor moieties are generally chosen for (a) high efficiency Foerster energy transfer; (b) a large final Stokes shift (>100 nm); (c) shift of the emission as far as possible into the red portion of the visible spectrum (>600 nm); and (d) shift of the emission to a higher wavelength than the Raman water fluorescent emission produced by excitation at the donor excitation wavelength. For example, a donor fluorescent moiety can be chosen that has its excitation maximum near a laser line (for example, helium-cadmium 442 nm or Argon 488 nm), a high extinction coefficient, a high quantum yield, and a good overlap of its fluorescent emission with the excitation spectrum of the corresponding acceptor fluorescent moiety. A corresponding acceptor fluorescent moiety can be chosen that has a high extinction coefficient, a high quantum yield, a good overlap of its excitation with the emission of the donor fluorescent moiety, and emission in the red part of the visible spectrum (>600 nm).

Representative donor fluorescent moieties that can be used with various acceptor fluorescent moieties in FRET technology include fluorescein, Lucifer Yellow, B-phycoerythrin, 9-acridineisothiocyanate, Lucifer Yellow VS, 4-acetamido-4'-isothio-cyanatostilbene-2,2'-disulfonic acid, 7-di ethylamino-3-(4 '-isothiocyanatophenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC Red 640, LC Red 705, Cy5, Cy5.5, Lissamine rhodamine B sulfonyl chloride, tetramethyl rhodamine isothiocyanate, rhodamine x isothiocyanate, erythrosine isothiocyanate, fluorescein, diethylenetriamine pentaacetate, or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

The donor and acceptor fluorescent moieties can be attached to the appropriate probe oligonucleotide via a linker arm. The length of each linker arm is important, as the linker arms will affect the distance between the donor and acceptor fluorescent moieties. The length of a linker arm can be the distance in Angstroms (Å) from the nucleotide base to the fluorescent moiety. In general, a linker arm is from about 10 Å to about 25 Å. The linker arm may be of the kind described in International Patent Publication No. WO 84/03285. WO 84/03285 also discloses methods for attaching linker arms to a particular nucleotide base, and also for attaching fluorescent moieties to a linker arm.

An acceptor fluorescent moiety, such as an LC Red 640, can be combined with an oligonucleotide that contains an amino linker (e.g., C6-amino phosphoramidites available from ABI (Foster City, Calif.) or Glen Research (Sterling, VA)) to produce, for example, LC Red 640-labeled oligonucleotide. Frequently used linkers to couple a donor fluorescent moiety such as fluorescein to an oligonucleotide include thiourea linkers (FITC-derived, for example, fluorescein-CPG's from Glen Research or ChemGene (Ashland, Mass.)), amide-linkers (fluorescein-NHS-ester-derived, such as CX-fluorescein-CPG from BioGenex (San Ramon, Calif)), or 3'-amino-CPGs that require coupling of a fluorescein-NHS-ester after oligonucleotide synthesis.

Detection of *Plasmodium* Amplified Product (Amplicon)

The present disclosure provides methods for detecting the presence or absence of Malaria parasites (including *Plasmodium*) in a biological or non-biological sample. Methods provided avoid problems of sample contamination, false negatives, and false positives. The methods include performing at least one cycling step that includes amplifying a portion of *Plasmodium* target nucleic acid molecules from a sample using one or more pairs of *Plasmodium* primers, and a FRET detecting step. Multiple cycling steps are performed, preferably in a thermocycler. Methods can be performed using the *Plasmodium* primers and probes to detect the presence of *Plasmodium*, and the detection of *Plasmodium* indicates the presence of *Plasmodium* in the sample.

As described herein, amplification products can be detected using labeled hybridization probes that take advantage of FRET technology. One FRET format utilizes TaqMan® technology to detect the presence or absence of an amplification product, and hence, the presence or absence of Malaria parasites (including *Plasmodium*). TaqMan® technology utilizes one single-stranded hybridization probe labeled with, e.g., one fluorescent moiety or dye (e.g., HEX or FAM) and one quencher (e.g., BHQ-2), which may or may not be fluorescent. When a first fluorescent moiety is excited with light of a suitable wavelength, the absorbed energy is transferred to a second fluorescent moiety or a dark quencher according to the principles of FRET. The second moiety is generally a quencher molecule. During the annealing step of the PCR reaction, the labeled hybridization probe binds to the target DNA (i.e., the amplification product) and is degraded by the 5' to 3' nuclease activity of, e.g., the Taq Polymerase during the subsequent elongation phase. As a result, the fluorescent moiety and the quencher moiety become spatially separated from one another. As a consequence, upon excitation of the first fluorescent moiety in the absence of the quencher, the fluorescence emission from the first fluorescent moiety can be detected. By way of example, an ABI PRISM® 7700 Sequence Detection System (Applied Biosystems) uses TaqMan® technology, and is suitable for performing the methods described herein for detecting the presence or absence of Malaria parasites (including *Plasmodium*) in the sample.

Molecular beacons in conjunction with FRET can also be used to detect the presence of an amplification product using the real-time PCR methods. Molecular beacon technology uses a hybridization probe labeled with a first fluorescent moiety and a second fluorescent moiety. The second fluorescent moiety is generally a quencher, and the fluorescent labels are typically located at each end of the probe. Molecular beacon technology uses a probe oligonucleotide having sequences that permit secondary structure formation (e.g., a hairpin). As a result of secondary structure formation within the probe, both fluorescent moieties are in spatial proximity when the probe is in solution. After hybridization to the target nucleic acids (i.e., amplification products), the secondary structure of the probe is disrupted and the fluorescent moieties become separated from one another such that after excitation with light of a suitable wavelength, the emission of the first fluorescent moiety can be detected.

Another common format of FRET technology utilizes two hybridization probes. Each probe can be labeled with a different fluorescent moiety and are generally designed to hybridize in close proximity to each other in a target DNA molecule (e.g., an amplification product). A donor fluorescent moiety, for example, fluorescein, is excited at 470 nm by the light source of the LightCycler® Instrument. During FRET, the fluorescein transfers its energy to an acceptor fluorescent moiety such as LightCycler®-Red 640 (LC Red 640) or LightCycler®-Red 705 (LC Red 705). The acceptor fluorescent moiety then emits light of a longer wavelength, which is detected by the optical detection system of the LightCycler® instrument. Efficient FRET can only take place when the fluorescent moieties are in direct local proximity and when the emission spectrum of the donor fluorescent moiety overlaps with the absorption spectrum of the acceptor fluorescent moiety. The intensity of the emitted signal can be correlated with the number of original target DNA molecules (e.g., the number of *Plasmodium* genomes). If amplification of *Plasmodium* target nucleic acid occurs and an amplification product is produced, the step of hybridizing results in a detectable signal based upon FRET between the members of the pair of probes.

Generally, the presence of FRET indicates the presence of *Plasmodium* in the sample, and the absence of FRET indicates the absence of *Plasmodium* in the sample. Inadequate specimen collection, transportation delays, inappropriate transportation conditions, or use of certain collection swabs (calcium alginate or aluminum shaft) are all conditions that can affect the success and/or accuracy of a test result, however.

Representative biological samples that can be used in practicing the methods include, but are not limited to whole blood, respiratory specimens, urine, fecal specimens, blood specimens, plasma, dermal swabs, nasal swabs, wound swabs, blood cultures, skin, and soft tissue infections. Collection and storage methods of biological samples are known to those of skill in the art. Biological samples can be processed (e.g., by nucleic acid extraction methods and/or kits known in the art) to release *Plasmodium* nucleic acid or in some cases, the biological sample can be contacted directly with the PCR reaction components and the appropriate oligonucleotides. In some instances, the biological sample is whole blood. When whole blood is typically collected, it is often collected in vessels containing anticoagulants, such as heparin, citrate, or EDTA, which enables the whole blood to be stored at suitable temperatures. However, under such conditions, the nucleic acids within the whole blood undergo considerable amount of degradation. Therefore, it may be advantageous to collect the blood in a reagent that will lyse, denature, and stabilize whole blood components, including nucleic acids, such as a nucleic acid-stabilizing solution. In such cases, the nucleic acids can be better preserved and stabilized for subsequent isolation and analysis, such as by nucleic acid test, such as PCR. Such nucleic acid-stabilizing solution are well known in the art, including, but not limited to, cobas PCR media, which contains 4.2 M guanadinium salt (GuHCl) and 50 mM Tris, at a pH of 7.5.

The sample can be collected by any method or device designed to adequately hold and store the sample prior to analysis. Such methods and devices are well known in the art. In the case that the sample is a biological sample, such as whole blood, the method or device may include a blood collection vessel. Such a blood collection vessel is well known in the art, and may include, for example, a blood collection tube. In many cases, it may be advantageous to use a blood collection tube wherein the blood collection vessel is under pressure in the space intended for sample uptake, such as a blood vessel with an evacuated chamber, such as a vacutainer blood collection tube. Such blood collection tubes with an evacuated chamber, such as a vacutainer blood collection tube are well known in the art. It may further be advantageous to collect the blood in a blood collection vessel, with or without an evacuated chamber, that contains within it, a solution that will lyse, denature, and stabilize whole blood components, including nucleic acids, such as a nucleic acid-stabilizing solution, such that the whole blood being drawn immediately contacts the nucleic acid-stabilizing solution in the blood collection vessel.

Melting curve analysis is an additional step that can be included in a cycling profile. Melting curve analysis is based on the fact that DNA melts at a characteristic temperature called the melting temperature (Tm), which is defined as the temperature at which half of the DNA duplexes have separated into single strands. The melting temperature of a DNA depends primarily upon its nucleotide composition. Thus, DNA molecules rich in G and C nucleotides have a higher Tm than those having an abundance of A and T nucleotides. By detecting the temperature at which signal is lost, the melting temperature of probes can be determined. Similarly, by detecting the temperature at which signal is generated, the annealing temperature of probes can be determined. The melting temperature(s) of the *Plasmodium* probes from the *Plasmodium* amplification products can confirm the presence or absence of *Plasmodium* in the sample.

Within each thermocycler run, control samples can be cycled as well. Positive control samples can amplify target nucleic acid control template (other than described amplification products of target genes) using, for example, control primers and control probes. Positive control samples can also amplify, for example, a plasmid construct containing the target nucleic acid molecules. Such a plasmid control can be amplified internally (e.g., within the sample) or in a separate sample run side-by-side with the patients' samples using the same primers and probe as used for detection of the intended target. Such controls are indicators of the success or failure of the amplification, hybridization, and/or FRET reaction. Each thermocycler run can also include a negative control that, for example, lacks target template DNA. Negative control can measure contamination. This ensures that the system and reagents would not give rise to a false positive signal. Therefore, control reactions can readily determine, for example, the ability of primers to anneal with sequence-specificity and to initiate elongation, as well as the ability of probes to hybridize with sequence-specificity and for FRET to occur.

In an embodiment, the methods include steps to avoid contamination. For example, an enzymatic method utilizing uracil-DNA glycosylase is described in U.S. Pat. Nos. 5,035,996, 5,683,896 and 5,945,313 to reduce or eliminate contamination between one thermocycler run and the next.

Conventional PCR methods in conjunction with FRET technology can be used to practice the methods. In one embodiment, a LightCycler® instrument is used. The following patent applications describe real-time PCR as used in the LightCycler® technology: International Patent Publication Nos. WO 97/46707, WO 97/46714, and WO 97/46712.

The LightCycler® can be operated using a PC workstation and can utilize a Windows NT operating system. Signals from the samples are obtained as the machine positions the capillaries sequentially over the optical unit. The software can display the fluorescence signals in real-time immediately after each measurement. Fluorescent acquisition time is 10-100 milliseconds (msec). After each cycling step, a quantitative display of fluorescence vs. cycle number can be continually updated for all samples. The data generated can be stored for further analysis.

As an alternative to FRET, an amplification product can be detected using a double-stranded DNA binding dye such as a fluorescent DNA binding dye (e.g., SYBR® Green or SYBR® Gold (Molecular Probes)). Upon interaction with the double-stranded nucleic acid, such fluorescent DNA binding dyes emit a fluorescence signal after excitation with light at a suitable wavelength. A double-stranded DNA binding dye such as a nucleic acid intercalating dye also can be used. When double-stranded DNA binding dyes are used, a melting curve analysis is usually performed for confirmation of the presence of the amplification product.

One of skill in the art would appreciate that other nucleic acid- or signal-amplification methods may also be employed. Examples of such methods include, without limitation, branched DNA signal amplification, loop-mediated isothermal amplification (LAMP), nucleic acid sequence-based amplification (NASBA), self-sustained sequence replication (3 SR), strand displacement amplification (SDA), or smart amplification process version 2 (SMAP 2).

It is understood that the embodiments of the present disclosure are not limited by the configuration of one or more commercially available instruments.

Articles of Manufacture/Kits

Embodiments of the present disclosure further provide for articles of manufacture or kits to detect Malaria parasites (including *Plasmodium*). An article of manufacture can include primers and probes used to detect the *Plasmodium* gene target, together with suitable packaging materials. Representative primers and probes for detection of *Plasmodium* are capable of hybridizing to *Plasmodium* target nucleic acid molecules. In addition, the kits may also include suitably packaged reagents and materials needed for DNA immobilization, hybridization, and detection, such solid supports, buffers, enzymes, and DNA standards. Methods of designing primers and probes are disclosed herein, and representative examples of primers and probes that amplify and hybridize to *Plasmodium* target nucleic acid molecules are provided.

Articles of manufacture can also include one or more fluorescent moieties for labeling the probes or, alternatively, the probes supplied with the kit can be labeled. For example, an article of manufacture may include a donor and/or an acceptor fluorescent moiety for labeling the *Plasmodium* probes. Examples of suitable FRET donor fluorescent moieties and corresponding acceptor fluorescent moieties are provided above.

Articles of manufacture can also contain a package insert or package label having instructions thereon for using the *Plasmodium* primers and probes to detect *Plasmodium* in a sample. Articles of manufacture may additionally include reagents for carrying out the methods disclosed herein (e.g., buffers, polymerase enzymes, co-factors, or agents to prevent contamination). Such reagents may be specific for one of the commercially available instruments described herein.

Embodiments of the present disclosure also provide for a set of primers and one or more detectable probes for the detection of Malaria parasites (including *Plasmodium*) in a sample.

Embodiments of the present disclosure will be further described in the following examples, which do not limit the scope of the invention described in the claims.

EXAMPLES

The following examples and figures are provided to aid the understanding of the subject matter, the true scope of which is set forth in the appended claims. It is understood that modifications can be made in the procedures set forth without departing from the spirit of the invention.

The test was a fully automated sample preparation (nucleic acid extraction and purification) followed by PCR amplification and detection. The system used was the Cobas® 6800/8800 System, which consisted of a sample supply module, the transfer module, the processing module, and the analytic module.

Selective amplification of target nucleic acid was achieved by the use of specific forward and reverse primers which were selected from highly conserved regions of the target nucleic acid. A thermostable DNA polymerase enzyme was used for both reverse-transcription and amplification. The master mix included deoxyuridine triphosphate (dUTP), instead of deoxythimidine triphosphate (dTTP), which is incorporated into the newly synthesized DNA (amplified product or amplicon). Any contaminating amplicons from previous PCR runs were destroyed by the AmpErase enzyme (uracil-N-glycosylase), which was included in the PCR mix, when heated in the first thermal cycling step. Newly formed amplicons were not destroyed, however, since the AmpErase enzyme was inactivated once exposed to temperatures above 55° C.

The Cobas® *Plasmodium* master mix contained detection probes which were specific for *Plasmodium* and control nucleic acids. The specific *Plasmodium* and control detection probes were each labeled with one of two unique fluorescent dyes which act as a reporter. Each probe also had a second dye which acted as a quencher. The reporter dye is measured at a defined wavelength, thus permitting detection and discrimination of the amplified *Plasmodium* target and the control. The fluorescent signal of the intact probes was suppressed by the quencher dye. During the PCR amplification step, hybridization of the probes to the specific single-stranded DNA template resulted in cleavage by the 5' to 3' nuclease activity of the DNA polymerase resulting in separation of the reporter and quencher dyes, and the generation of fluorescent signal. With each PCR cycle, increasing amounts of cleaved probes were generated and the cumulative signal of the reporter dye was concomitantly increased. Because the two specific reporter dyes are measured at defined wavelengths, simultaneous detection and discrimination of the amplified *Plasmodium* target and the control was possible.

The primers and probes for the *Plasmodium* test were designed by seeding primers and probes along the genome in the most conserved regions based on the alignment. The primers and probes were then combined into assays and the assays were scored based on the inclusivity and exclusivity in-silico assessment. In addition to genomic conservation, genomic coverage (which is highly dependent on what sequences are available publicly) was also included in the scoring of the assays. The targeted region of the *Plasmodium* genome was the Mitochondrial DNA Targets (MT-1 and MT-2), RNA repeat sequence R125, and 18S ribosomal RNA. The disclosed Malaria parasite assay is designed to be a pan-Malaria assay, which is able to detect the following *Plasmodium* species: *P. falciparum, P. vivax, P. malariae, P. ovale*, and *P. knowlesi*. The assay excludes target sequences that share homology with closely related species (e.g., parasites and bacteria) and humans, as well as environmental DNA that may be found in the various assay reagents. The Malaria assay is designed to detect *Plasmodium* species in samples, such as biological samples, such as whole blood. The disclosed Malaria assay detects *Plasmodium* species in about 1.1 ml of whole blood. In some circumstances, the whole blood sample is in a tube/vessel, such as an evacuated tube/vessel that also contains within it, a reagent/solution that will lyse, denature, and stabilize whole blood components, including nucleic acids, such as a nucleic acid-stabilizing solution, such that the whole blood being drawn immediately contacts the nucleic acid-stabilizing solution in the blood collection vessel. The disclosed primer pairs having a nucleic acid sequences of SEQ ID NOs:16 and 17, and the disclosed probes having a nucleic acid sequence of SEQ ID NOs:18-20, detect and/or amplify the Mitochondrial DNA target MT-1. The disclosed primers having a nucleic acid sequences of SEQ ID NOs:11-14, and the disclosed probe having a nucleic acid sequence of SEQ ID NO:15, detect and/or amplify the Mitochondrial DNA target MT-2. The disclosed primer pairs having a nucleic acid sequences of SEQ ID NOs:21, 22, and 26, and the disclosed probes having a nucleic acid sequences of SEQ ID NOs: 23-25, detect and/or amplify the RNA repeat sequence R125. The disclosed primer pairs having a nucleic acid sequences of SEQ ID NOs:1 and 2, and the disclosed probes having a nucleic acid sequence of SEQ ID NOs:3 and/or 4, detect and/or amplify the 18S ribosomal RNA target 18S-1. The disclosed primer pairs having a nucleic acid sequences of SEQ ID NOs:5 and 6, and the disclosed probe having a nucleic acid sequence of SEQ ID NO:7, detect and/or amplify the 18S ribosomal RNA target 18S-3. The disclosed primer pairs having a nucleic acid sequences of SEQ ID NOs:8 and 9, and the disclosed probe having a nucleic acid sequence of SEQ ID NO:10, detect and/or amplify the 18S ribosomal RNA target 18S-4.

Example 1: Amplification and Detection of *P. falciparum* by Real-Time PCR

The *Plasmodium* nucleic acid assay was tested using *P. falciparum* from *P. falciparum* cultures from ATCC (Catalog No. 30930), and was tested on all targets (18S rRNA gene (including 18S-1, 18S-3, 18S-4), Mitochondrial Gene (MT-1 and MT-2), and R-125, in singleplex format. The *Plasmodium* assay was tested at six different dilution levels of *P. falciparum*: neat, 1:10, 1:$10^2$, 1:$10^3$, 1:$10^4$, and 1:$10^5$. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is depicted in Table 2, below:

TABLE 2

| cobas ® 6800/8800 PCR Profile | | | | |
|---|---|---|---|---|
| Step | Cycles | Target (° C.) | Hold time (hh:mm:ss) | Ramp |
| Pre-PCR | 1 | 50 | 00:02:00 | 4.4 |
| | | 94 | 00:00:05 | 4.4 |
| | | 55 | 00:02:00 | 2.2 |
| | | 60 | 00:06:00 | 4.4 |
| | | 65 | 00:04:00 | 4.4 |
| 1. Meas | 5 | 95 | 00:00:05 | 4.4 |
| | | 55 | 00:00:30 | 2.2 |
| 2. Meas | 45 | 91 | 00:00:05 | 4.4 |
| | | 58 | 00:00:25 | 2.2 |
| Post | 1 | 40 | 00:02:00 | 2.2 |

Figure 2A:
FIGS. 2A-2F shows real time PCR growth curves of the *Plasmodium* assay using *P. falciparum* from *P. falciparum* cultures at six different dilution levels (neat, 1:10, 1:$10^2$, 1:$10^3$, 1:$10^4$, and 1:$10^5$).
Figure 2B:
Figure 2C:
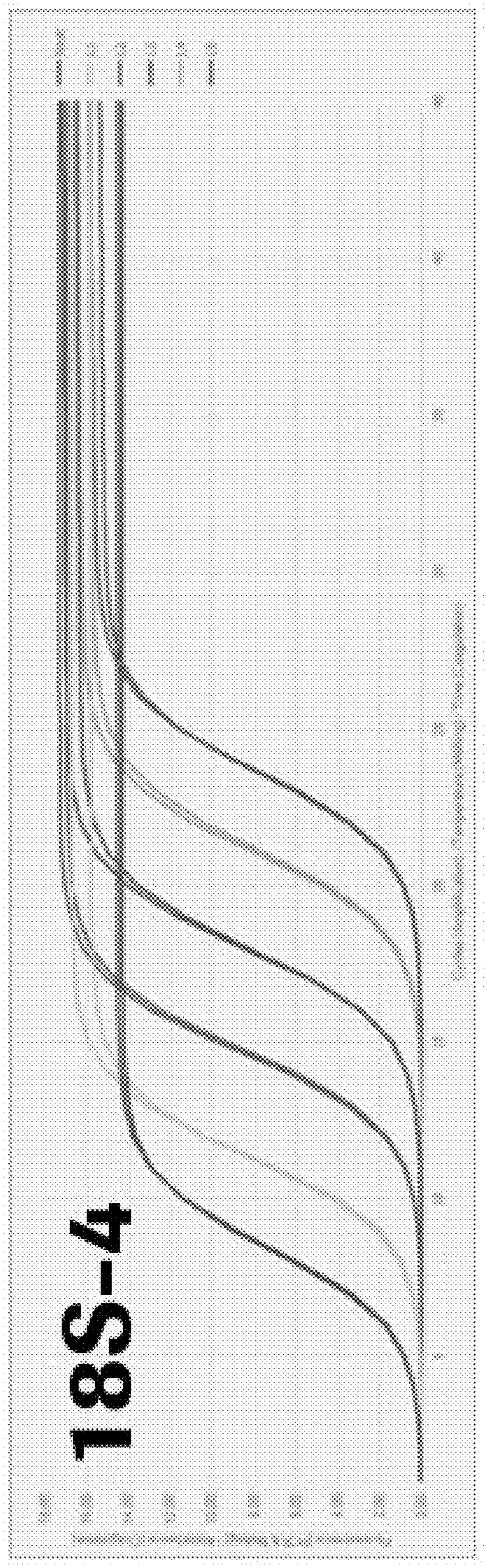
Figure 2D:
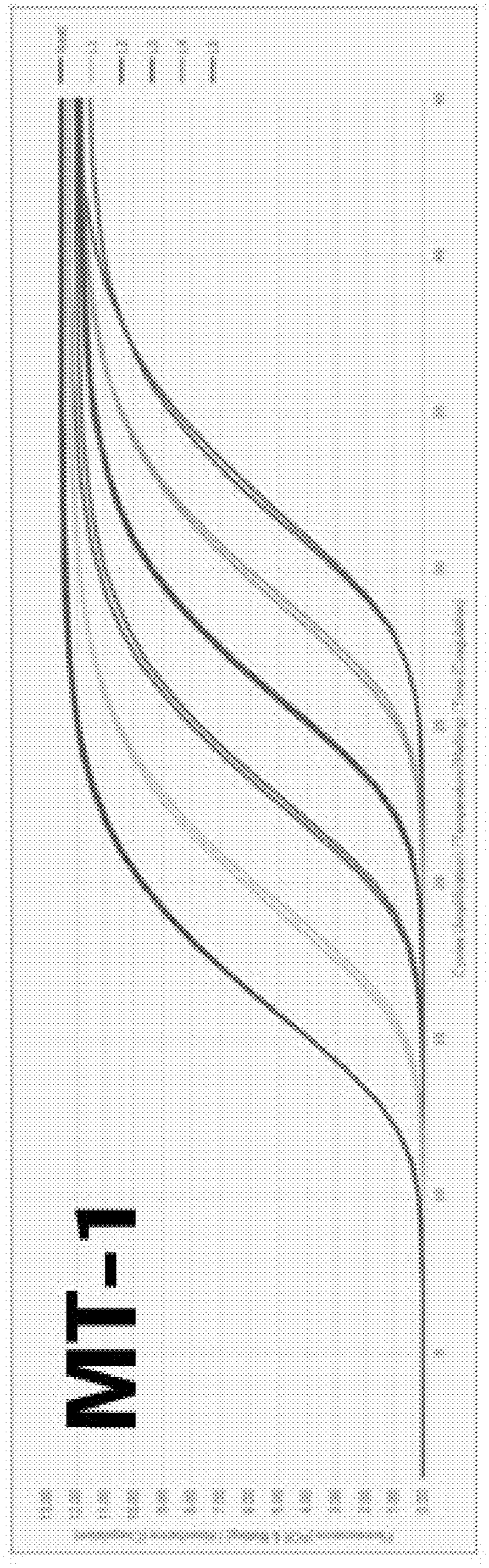
Figure 2E:
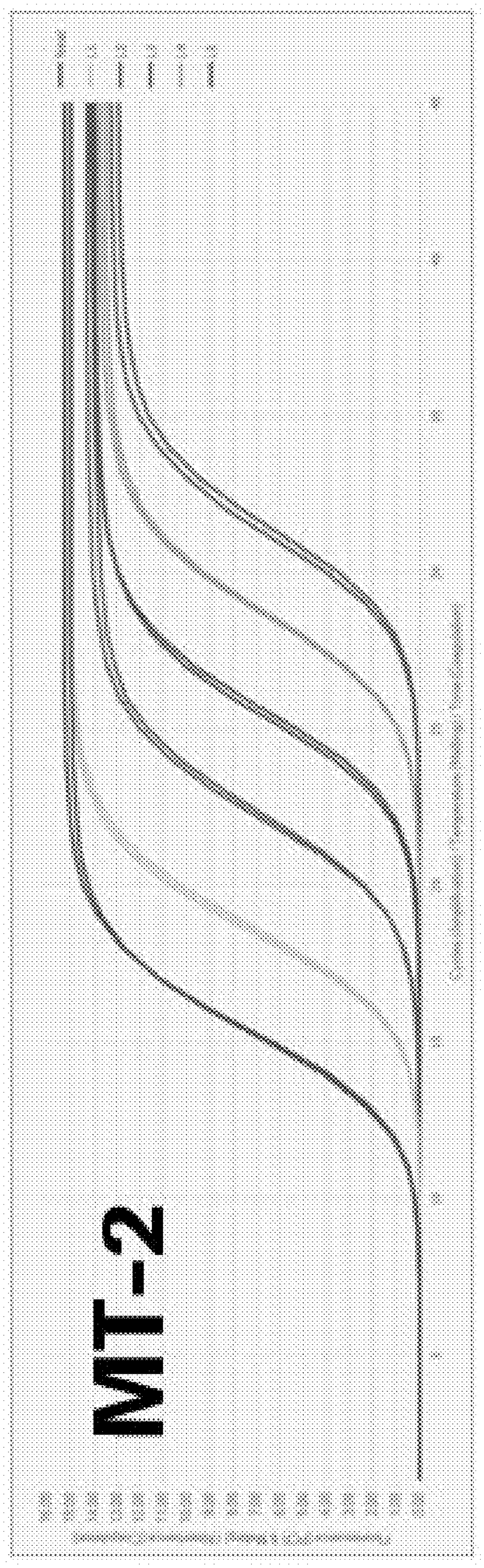
Figure 2F:

The studies for the 18S-1 target employed the primers having a nucleic acid sequence of SEQ ID NOs:1 and 2, and probe having a nucleic acid sequence of SEQ ID NO:3, and the results are shown in FIG. 2A. The studies for the 18S-3 target employed the primers having a nucleic acid sequence of SEQ ID NOs:5 and 6, and probe having a nucleic acid sequence of SEQ ID NO:7, and the results are shown in FIG. 2B. The studies for the 18S-4 target employed the primers having a nucleic acid sequence of SEQ ID NOs:8 and 9, and probe having a nucleic acid sequence of SEQ ID NO:10, and the results are shown in FIG. 2C. The studies for the MT-1 target employed the primers having a nucleic acid sequence of SEQ ID NOs:16 and 17, and probe having a nucleic acid sequence of SEQ ID NO:18, and the results are shown in FIG. 2D. The studies for the MT-2 target employed the primers having a nucleic acid sequence of SEQ ID NOs:11 and 12, and probe having a nucleic acid sequence of SEQ ID NO:15, and the results are shown in FIG. 2E. The studies for the R125 target employed the primers having a nucleic acid sequence of SEQ ID NOs:21 and 22, and probe having a nucleic acid sequence of SEQ ID NO:23, and the results are shown in FIG. 2F. FIGS. 2A-2F and FIG. 3 show that all targets were detected at all dilution levels tested. FIG. 3 shows a compilation of the data for the eluates at the 1:$10^5$ dilution level.

Figure 4:
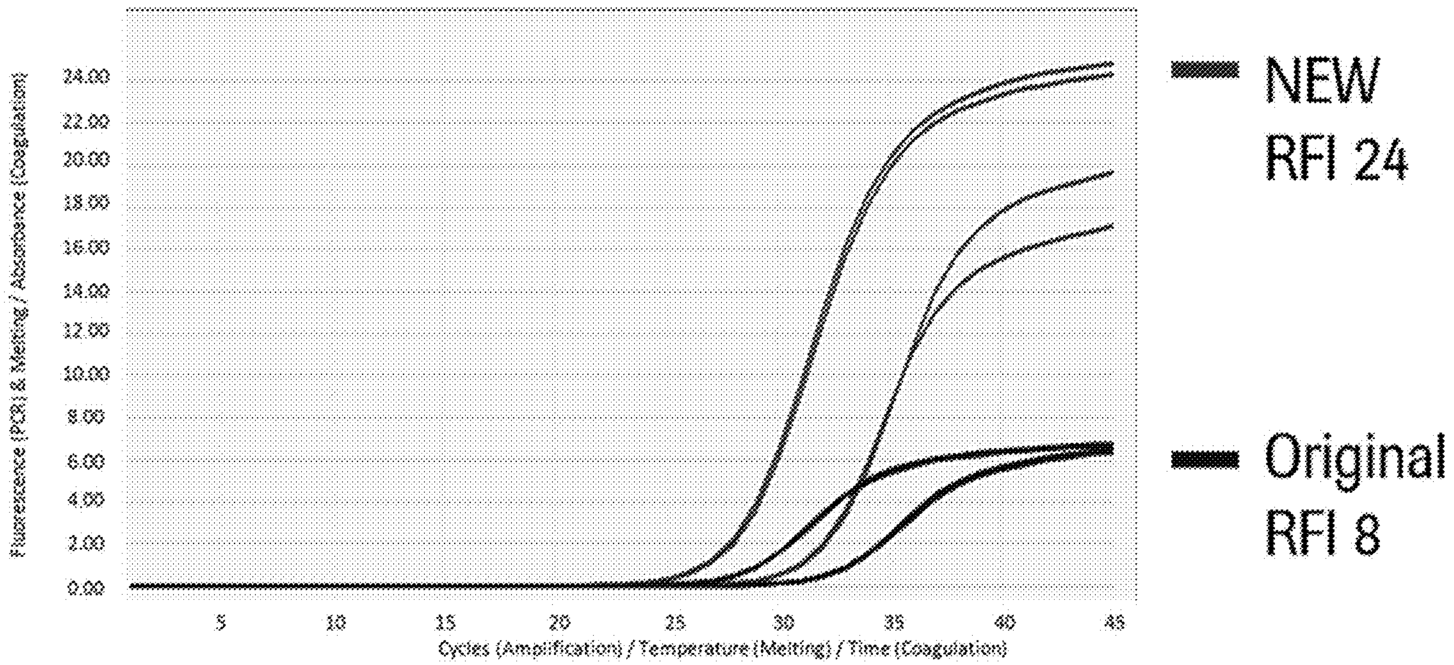
FIG. 4 shows real time PCR growth curves of the *Plasmodium* assay using *P. falciparum* from *P. falciparum* cultures for the 18S-1 target using a re-designed probe (SEQ ID NO:4), as described in Example 1. The curves using the original 18S-1 probe (SEQ ID NO:3) are shown in blue, and the curves using the re-designed 18S-1 probe (SEQ ID NO:4) are shown in red. All primers employed have a nucleic acid sequence of SEQ ID NOs:1 and 2.

In an effort to improve the RFI signal for the 18S-1 target, the probe was redesigned to increase the $T_m$. To that end, additional studies for the 18S-1 target were run, this time employing the primers having a nucleic acid sequence of SEQ ID NOs:1 and 2, and probe having a nucleic acid sequence of SEQ ID NO:4. A comparison of the results from the original 18S-1 probe (SEQ ID NO:3) against the revised 18S-1 probe (SEQ ID NO:4) was made, showing that the redesigned 18S-1 probe improved the RFI signal, with the results shown in FIG. 4.

Thus, these results demonstrate that the primers and probes of the *Plasmodium* assay are able to amplify and detect the presence of *P. falciparum* efficiently and specifically in a real-time PCR assay.

Example 2: Droplet Digital PCR (ddPCR) for Copy Number Quantification of *P. falciparum* Cultures Droplet digital PCR (ddPCR) assays were employed to determine stock target copy number of in vitro transcripts, DNA minigenes, and *Plasmodium* cultures, using *P. falciparum* from *P. falciparum* cultures from ATCC (Catalog No. 30930). The ddPCR assays tested all targets (18S rRNA gene (including 18S-1, 18S-3, 18S-4), Mitochondrial Gene (MT-1 and MT-2), and R-125, in singleplex format. The studies for the 18S-1 target employed the primers having a nucleic acid sequence of SEQ ID NOs:1 and 2, and probe having a nucleic acid sequence of SEQ ID NO:37. The studies for the 18S-3 target employed the primers having a nucleic acid sequence of SEQ ID NOs:5 and 6, and probe having a nucleic acid sequence of SEQ ID NO:38. The studies for the 18S-4 target employed the primers having a nucleic acid sequence of SEQ ID NOs:8 and 9, and probe having a nucleic acid sequence of SEQ ID NO:39. The studies for the MT-1 target employed the primers having a nucleic acid sequence of SEQ ID NOs:16 and 17, and probe having a nucleic acid sequence of SEQ ID NO:42. The studies for the MT-2 target employed the primers having a nucleic acid sequence of SEQ ID NOs:11 and 12, and probe having a nucleic acid sequence of SEQ ID NO:41. The studies for the R125 target employed the primers having a nucleic acid sequence of SEQ ID NOs:21 and 22, and probe having a nucleic acid sequence of SEQ ID NO:40. As in Example 1, the reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is depicted in Table 2, above.

The ddPCR results of the *P. falciparum* culture show that RNA targets greatly outnumber the DNA targets, and are shown in FIG. 5. The results show the copy number (per 11.1) of 1:$10^5$ culture dilution of *P. falciparum* cultures, which show high copy number of the 18S-1, 18S-4, and R125 targets, relative to the 18S-3, MT-1, and MT-2 targets.

Thus, these studies show a high copy number of the 18S-1, 18S-4, and R125 targets within the *P. falciparum* cultures.

Figure 6B:
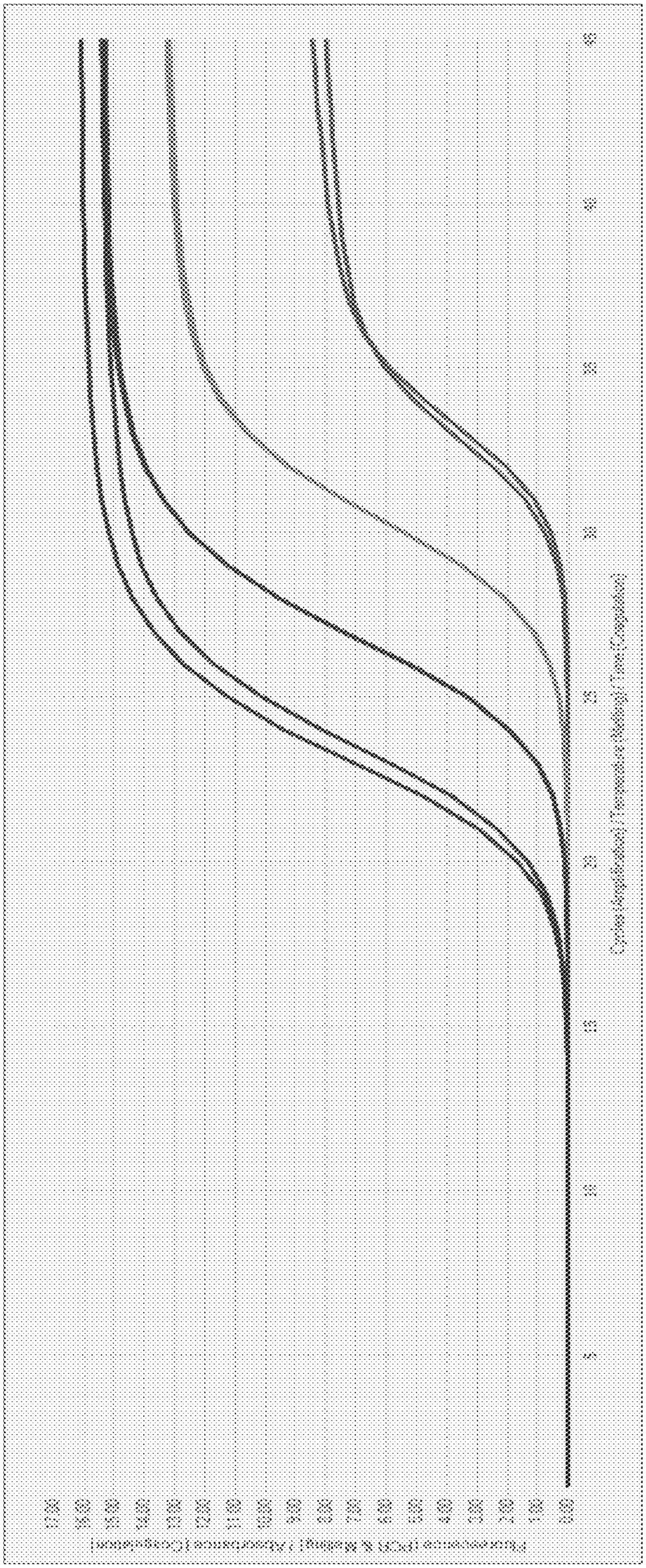
FIG. 6B shows the real time PCR growth curves from the multiplex assay with primers and probes for the 18S-1 and 18S-4 targets. For the 18S-1 target, this multiplex assay employed the primers having a nucleic acid sequence of SEQ ID NOs:1 and 2, and probe having a nucleic acid sequence of SEQ ID NO:4. For the 18S-4 target, this multiplex assay employed the primers having a nucleic acid sequence of SEQ ID NOs:8 and 9, and probe having a nucleic acid sequence of SEQ ID NO:10.

Example 3: Multiplex Amplification and Detection of 18S-1 and 18S-4 Targets in *P. falciparum* Culture by Real-Time PCR Because 18S-1 and 18S-4 were the highest expressed targets in the *P. falciparum* from *P. falciparum* cultures from ATCC (Catalog No. 30930) (see, Example 2, and FIG. 5), a multiplex assay was designed and developed to simultaneously amplify and detect the 18S-1 and 18S-4 targets (i.e., duplex) within the same sample. In particular, the 18S-1 and 18S-4 targets were tested as a multiplex to determine if the two 18S targets would improve sensitivity. In general, detection of multiple copy targets in parallel allows for increased sensitivity, and also mitigates the risk of any one singleplex assay failing by covering multiple targets. This multiplex assay was tested at four different dilution levels of *P. falciparum* (1:$10^4$, 1:$10^5$, 1:$10^6$, and 1:$10^7$), in a background of 500 ng of human whole blood genomic DNA/total RNA. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:1 and 2, and probe having a nucleic acid sequence of SEQ ID NO:4. For the 18S-4 target, this multiplex assay employed the primers having a nucleic acid sequence of SEQ ID NOs:8 and 9, and probe having a nucleic acid sequence of SEQ ID NO:10. The 18S-1 and 18S-4 targets were run in the FAM channel and the internal control (GIC) was run on the Cy5.5 channel. The data are shown in FIG. 6A, and the results are shown in FIG. 6B. In particular, FIGS. 6A and 6B shows that the Ct values for 18S-1 and 18S-4 are comparable, but that the RFI for 18S-1 is higher than that of 18S-4. These results show that the multiplex assay effectively and simultaneously amplifies and detects the 18S-1 and 18S-4 targets of *Plasmodium*. Studies on the impact of whole blood background on the multiplex assay did not identify any non-specific interactions and/or significant PCR inhibition issues (data not shown).

These studies demonstrate that the multiplex assay can successfully and effectively simultaneously amplify and detect the 18S-1 and 18S-4 targets of *Plasmodium.*

Figure 7B:
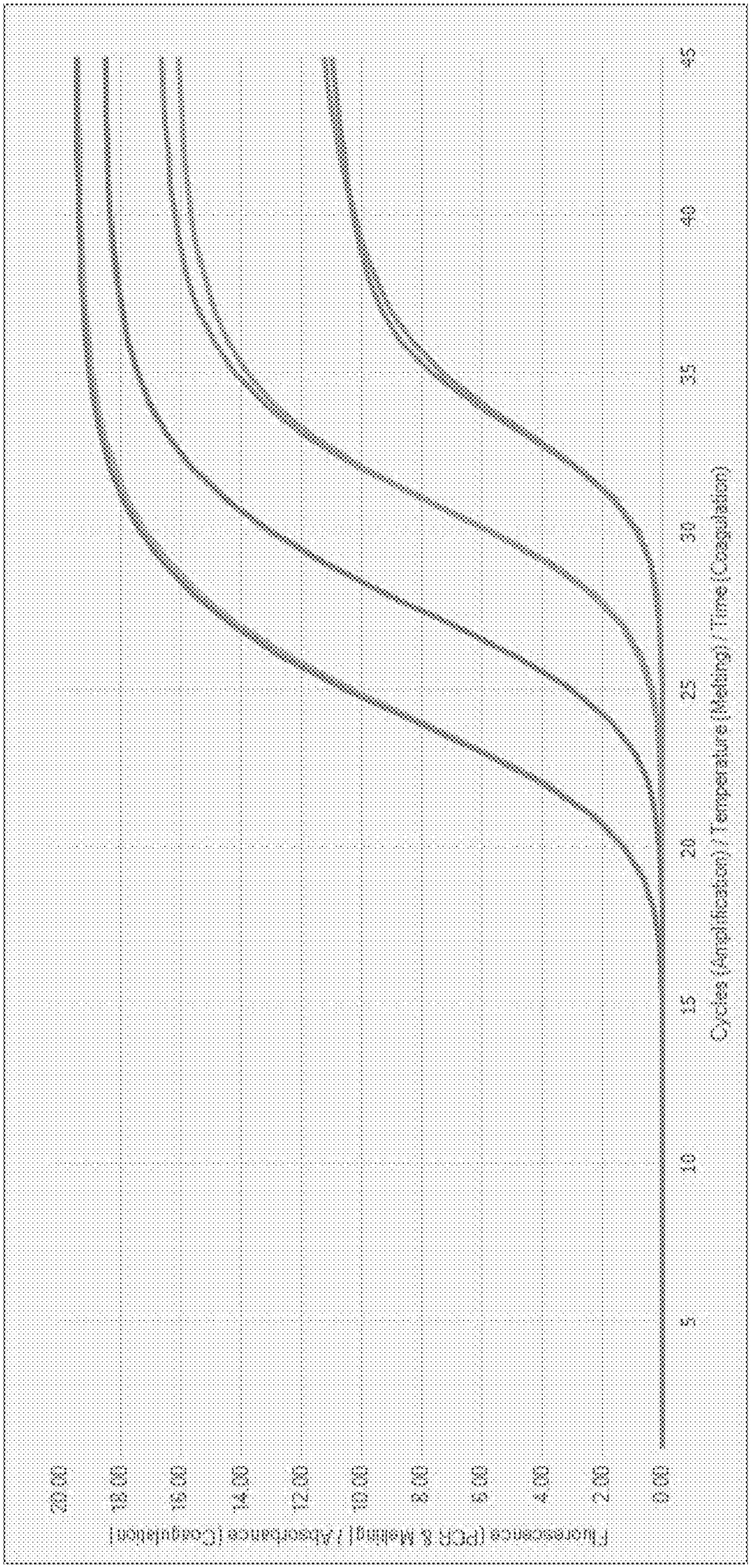
FIG. 7B shows the real time PCR growth curves from the multiplex assay with primers and probes for the 18S-1 and R125 targets. For the 18S-1 target, this multiplex assay employed the primers having a nucleic acid sequence of SEQ ID NOs:1 and 2, and probe having a nucleic acid sequence of SEQ ID NO:4. For the R125 target, this multiplex assay employed the primers having a nucleic acid sequence of SEQ ID NOs:21 and 22, and probe having a nucleic acid sequence of SEQ ID NO:25.

Example 4: Multiplex Amplification and Detection of 18S-1 and R125 Targets in *P. falciparum* Culture by Real-Time PCR A multiplex assay was designed and developed to simultaneously amplify and detect the 18S-1 target and the R125 target (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested at four different dilution levels of *P. falciparum* (1:$10^4$, 1:$10^5$, 1:$10^6$, and 1:$10^7$), in a background of 500 ng of whole blood genomic DNA. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:1 and 2, and probe having a nucleic acid sequence of SEQ ID NO:4. For the R125 target, this multiplex assay employed the primers having a nucleic acid sequence of SEQ ID NOs:21 and 22, and probe having a nucleic acid sequence of SEQ ID NO:25. The 18S-1 and R125 targets were run in the FAM channel and the internal control (GIC) was run on the Cy5.5 channel. The data are shown in FIG. 7A, and the results are shown in FIG. 7B. The data show that the Ct values for 18S-1 and R125 are comparable, but that the RFI for 18S-1 is higher than that of R125. These results show that the multiplex assay effectively and simultaneously amplifies and detects the 18S-1 and R125 targets of *Plasmodium*. Studies on the impact of whole blood background on the multiplex assay did not identify any non-specific interactions and/or significant PCR inhibition issues (data not shown).

These studies demonstrate that the multiplex assay can successfully and effectively simultaneously amplify and detect the 18S-1 and R125 targets of *Plasmodium.*

Example 5: Multiplex Amplification and Detection of 18S-1 and R125 Targets of In Vitro Transcripts in Whole Blood The multiplex assay that was designed and developed to simultaneously amplify and detect the 18S-1 target and the R125 target (i.e., duplex) within the same sample, and described in Example 4, above, was tested against in vitro transcripts of the 18S-1 and R125 targets and then added to DNA/RNA extracted from whole blood. As mentioned previously, in general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested at five different levels of in vitro transcripts of 18S-1 and R125: $10^5$, $10^4$, $10^3$, $10^2$, and 10 copies) in a background of 500 ng of whole blood genomic DNA/RNA. The copy numbers of the in vitro transcript stocks of 18S-1 and R125 transcripts was quantified by ddPCR. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:1 and 2, and probe having a nucleic acid sequence of SEQ ID NO:4. For the R125 target, this multiplex assay employed the primers having a nucleic acid sequence of SEQ ID NOs:21 and 22, and probe having a nucleic acid sequence of SEQ ID NO:25. The 18S-1 and R125 targets were run in the FAM channel and the internal control (GIC) was run on the Cy5.5 channel. The multiplex assay was also run separately as singleplex assays, for comparison. The data are shown in FIG. 8, which shows the multiplex and singleplex assays were sensitive down to 10 copies of input. Studies on the impact of whole blood background on the multiplex assay did not identify any non-specific interactions and/or significant PCR inhibition issues (data not shown).

These studies demonstrate that the multiplex assay can successfully and effectively simultaneously amplify and detect the 18S-1 and R125 targets of *Plasmodium.*

Figure 9:
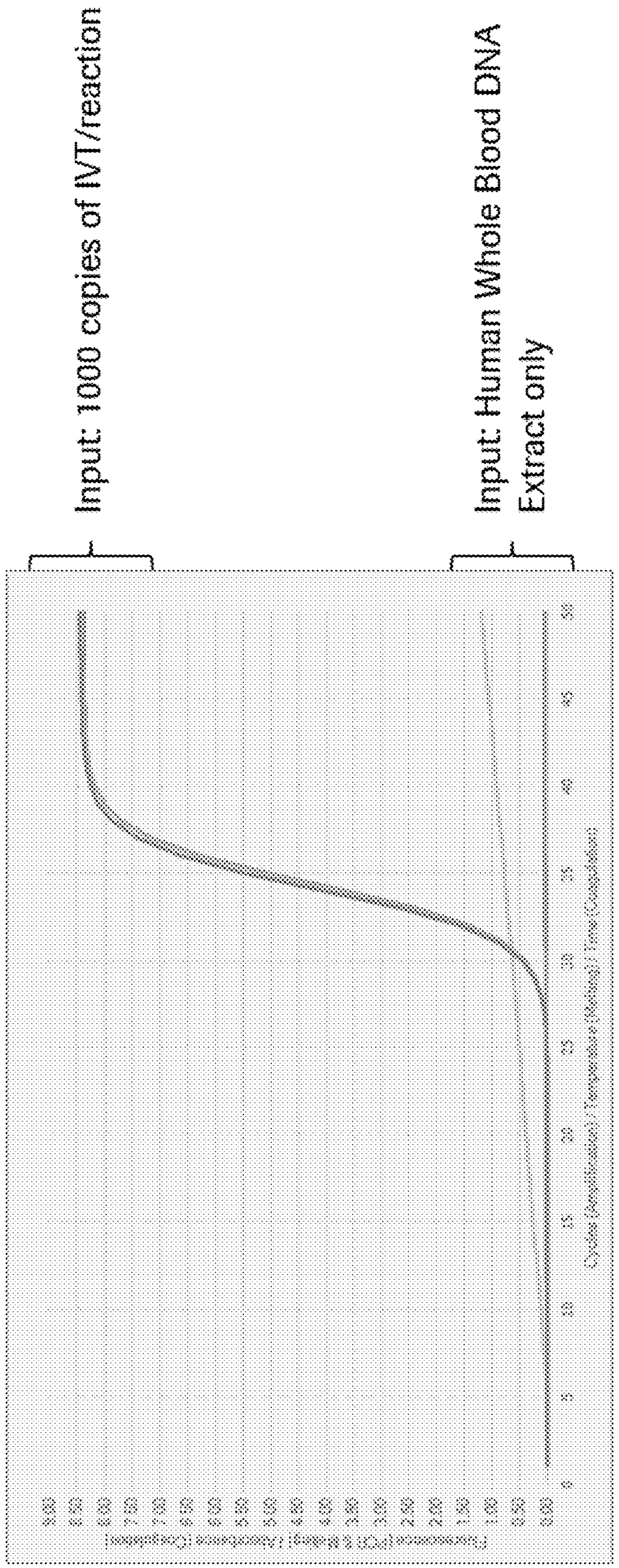
FIG. 9 shows the real time PCR growth curves from a singleplex assay using primers (SEQ ID NOs:22 and 26) and probe (SEQ ID NO:25) to amplify and detect in vitro transcripts of the R125 target (at $10^3$ copies), in a background of 500 ng of whole blood genomic DNA/RNA. The forward primer has a nucleic acid sequence of SEQ ID NO:26, the reverse primer has a nucleic acid sequence of SEQ ID NO:22, and the probe has a nucleic acid sequence of SEQ ID NO:25.

Example 6: Amplification and Detection of R125 Target of In Vitro Transcripts in Whole Blood In a singleplex assay for the R125 target, a new redesigned forward primer was tested against in vitro transcripts of the R125 target (at $10^3$ copies) and then added to DNA/RNA extracted from whole blood. The forward primer has a nucleic acid sequence of SEQ ID NO:26, the reverse primer has a nucleic acid sequence of SEQ ID NO:22, and the probe has a nucleic acid sequence of SEQ ID NO:25. The copy numbers of the in vitro transcript stocks of R125 transcripts was quantified by ddPCR, as above. The R125 target was run on the FAM channel and the internal control (GIC) was run on the Cy5.5 channel. The results are shown in FIG. 9, which shown that the redesigned oligonucleotide set (SEQ ID NOs:22, 25, and 26) are able to amplify and detect R125 targets from Malaria parasites, including *Plasmodium.*

These studies demonstrate that the singleplex assay can successfully and effectively amplify and detect the R125 target of *Plasmodium.*

Figure 10B:
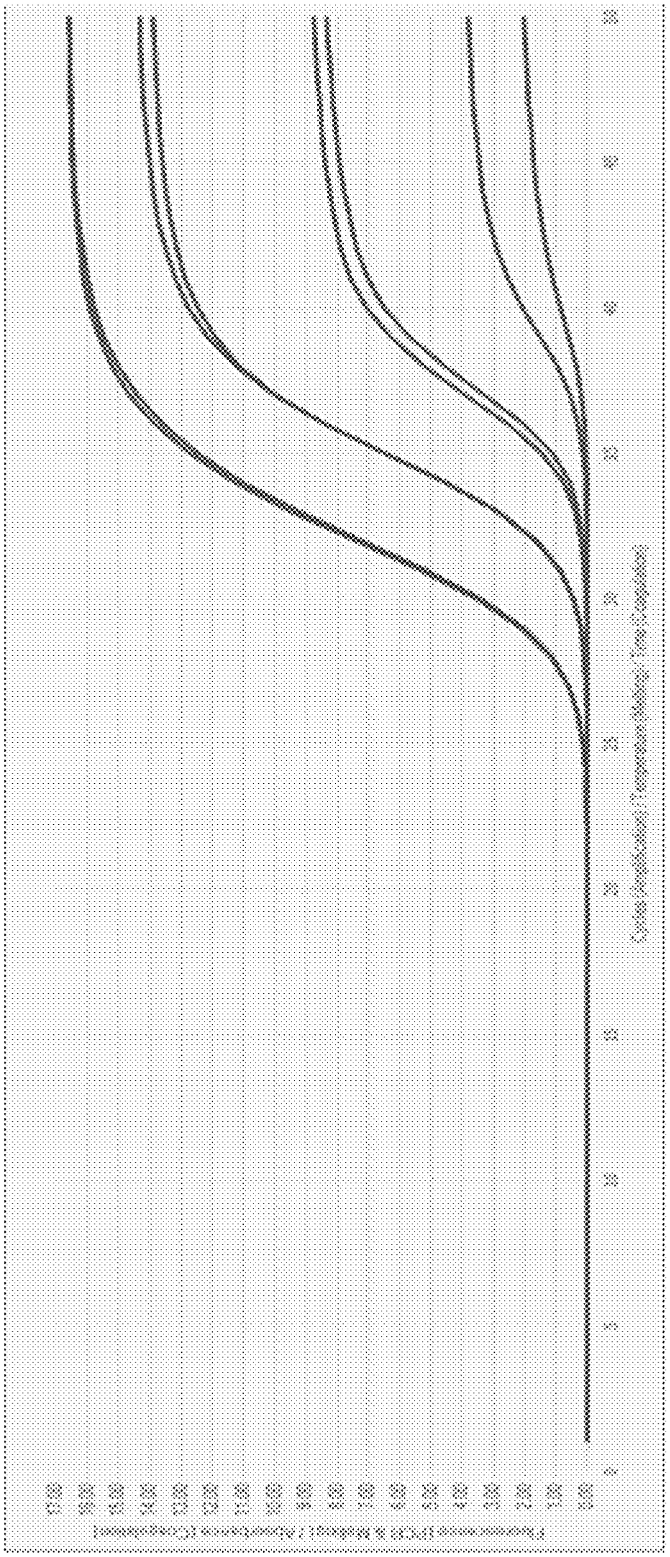
FIG. 10B shows the real time PCR growth curves from the multiplex assay with primers and probes for the 18S-1 and R125 targets. For the 18S-1 target, this multiplex assay employed the primers having a nucleic acid sequence of SEQ ID NOs:34 and 36, and probe having a nucleic acid sequence of SEQ ID NO:4. For the R125 target, this multiplex assay employed the primers having a nucleic acid sequence of SEQ ID NOs:27 and 22, and probe having a nucleic acid sequence of SEQ ID NO:25.

Example 7: Multiplex Amplification and Detection of 18S-1 and R125 Targets in *P. falciparum* Culture by Real-Time PCR A multiplex assay was designed and developed to simultaneously amplify and detect the 18S-1 target and the R125 target (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested at four different dilution levels of *P. falciparum* (1:$10^4$, 1:$10^5$, 1:$10^6$, and 1:$10^7$), in a background of whole blood nucleic acids that were extracted on the Cobas® 6800/8800 instrument. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34 and 36, and probe having a nucleic acid sequence of SEQ ID NO:4. For the R125 target, this multiplex assay employed the primers having a nucleic acid sequence of SEQ ID NOs:22 and 27, and probe having a nucleic acid sequence of SEQ ID NO:25. The 18S-1 and R125 targets were run in the FAM channel and the internal control (GIC) was run on the Cy5.5 channel. The data are shown in FIG. 10A, and the results are shown in FIG. 10B. The data show that the Ct values for 18 S-1 and R125 are comparable, but that the RFI for 18 S-1 is higher than that of R125. These results show that the multiplex assay effectively and simultaneously amplifies and detects the 18S-1 and R125 targets of *Plasmodium*. Studies on the impact of whole blood background on the multiplex assay did not identify any non-specific interactions and/or significant PCR inhibition issues (data not shown).

These studies demonstrate that the multiplex assay can successfully and effectively simultaneously amplify and detect the 18S-1 and R125 targets of *Plasmodium.*

Figure 11:
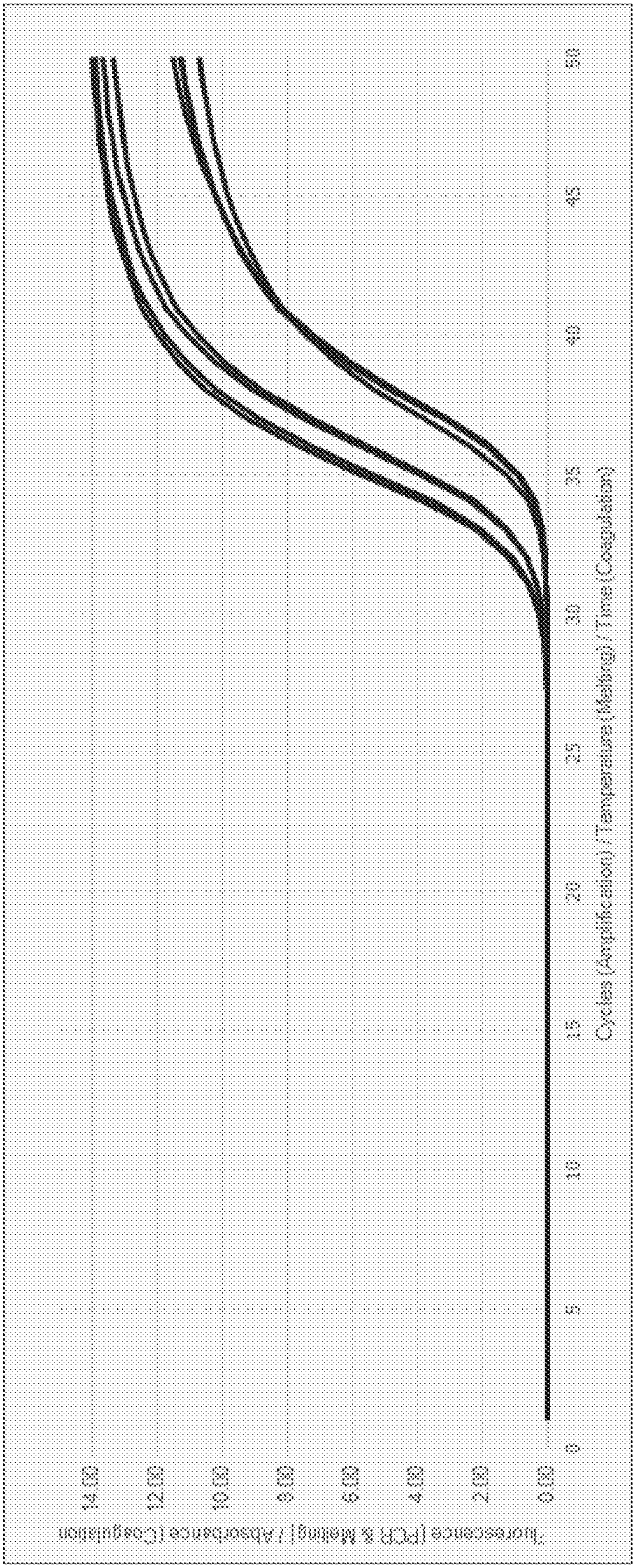
FIG. 11 shows the real time PCR growth curves from the multiplex assay with primers and probes for the 18S-1 and 18S-3 targets, using *P. falciparum* from *P. falciparum* cultures at two different dilution levels (1:$10^4$ and 1:$10^5$), in a background of whole blood nucleic acids that were extracted on the cobas 6800 instrument. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and probe having a nucleic acid sequence of SEQ ID NO:58.

Example 8: Multiplex Amplification and Detection of 18S-1 and 18S-3 Targets in *P. falciparum* Culture by Real-Time PCR A multiplex assay was designed and developed to simultaneously amplify and detect the two targets with the 18S rRNA region (18S-1 and 18S-3) (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested at two different dilution levels of *P. falciparum* (1:$10^4$ and 1:$10^5$), in a background of whole blood nucleic acids that were extracted on the Cobas® 6800/8800 instrument. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and a probe having a nucleic acid sequence of SEQ ID NO:58. The 18S-1 and 18S-3 targets were run in the FAM channel and the internal control (GIC) was run on the Cy5.5 channel. The results of this 18S-1 and 18S-3 multiplex Malaria assay are shown in FIG. 11. These results show that the multiplex assay effectively and simultaneously amplifies and detects the 18S-1 and 18S-3 targets of *Plasmodium*. Studies on the impact of whole blood background on the multiplex assay did not identify any non-specific interactions and/or significant PCR inhibition issues (data not shown).

These studies demonstrate that the dual target multiplex assay can successfully and effectively simultaneously amplify and detect the 18S rRNA (18S-1 and 18S-3 targets) region of *Plasmodium.*

Figure 12:
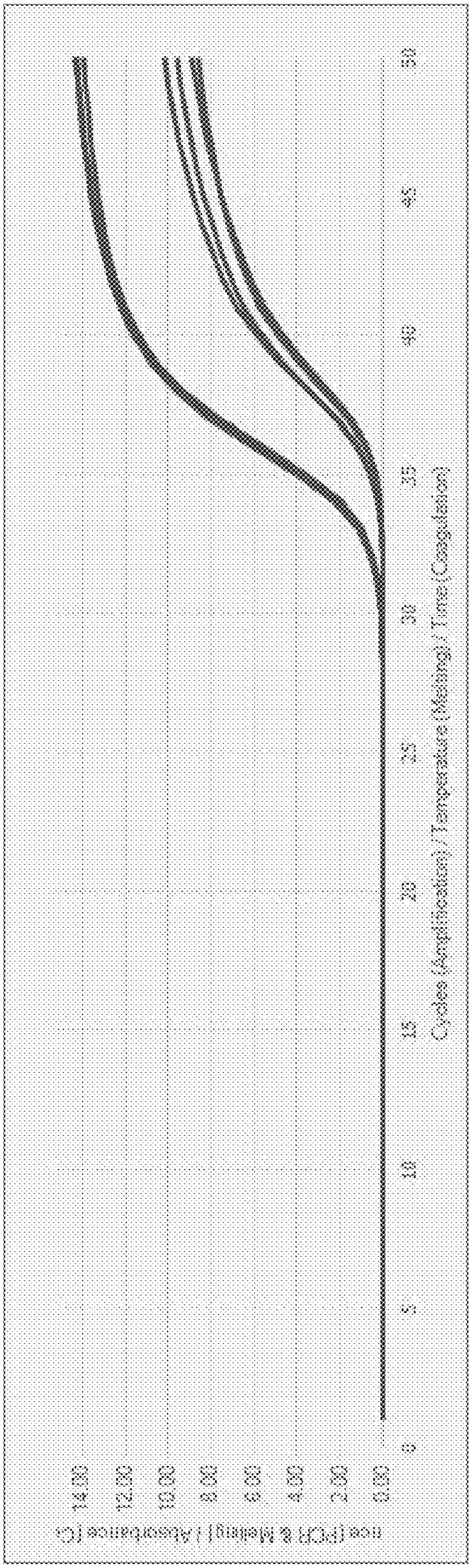
FIG. 12 shows the real time PCR growth curves from the multiplex assay with primers and probes for the 18S-1 and 18S-3 targets, using *P. vivax* from *P. vivax* cultures at two different dilution levels (1:$10^3$ and 1:$10^4$), in a background of whole blood nucleic acids that were extracted on the cobas 6800 instrument. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and probe having a nucleic acid sequence of SEQ ID NO:58.

Example 9: Multiplex Amplification and Detection of 18S-1 and 18S-3 Targets in *P. vivax* Culture by Real-Time PCR A multiplex assay was designed and developed to simultaneously amplify and detect the two targets with the 18S rRNA region (18S-1 and 18S-3) (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested at four different dilution levels of *P. vivax* ($1:10^3$ and $1:10^4$), in a background of whole blood nucleic acids that were extracted on the Cobas® 6800/8800 instrument. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and a probe having a nucleic acid sequence of SEQ ID NO:58. The 18S-1 and 18S-3 targets were run in the FAM channel and the internal control (GIC) was run on the Cy5.5 channel. The results of this 18S-1 and 18S-3 multiplex Malaria assay are shown in FIG. 12. These results show that the multiplex assay effectively and simultaneously amplifies and detects the 18S-1 and 18S-3 targets of *Plasmodium*. Studies on the impact of whole blood background on the multiplex assay did not identify any non-specific interactions and/or significant PCR inhibition issues (data not shown).

These studies demonstrate that the dual target multiplex assay can successfully and effectively simultaneously amplify and detect the 18S rRNA (18S-1 and 18S-3 targets) region of *Plasmodium.*

Figure 13:
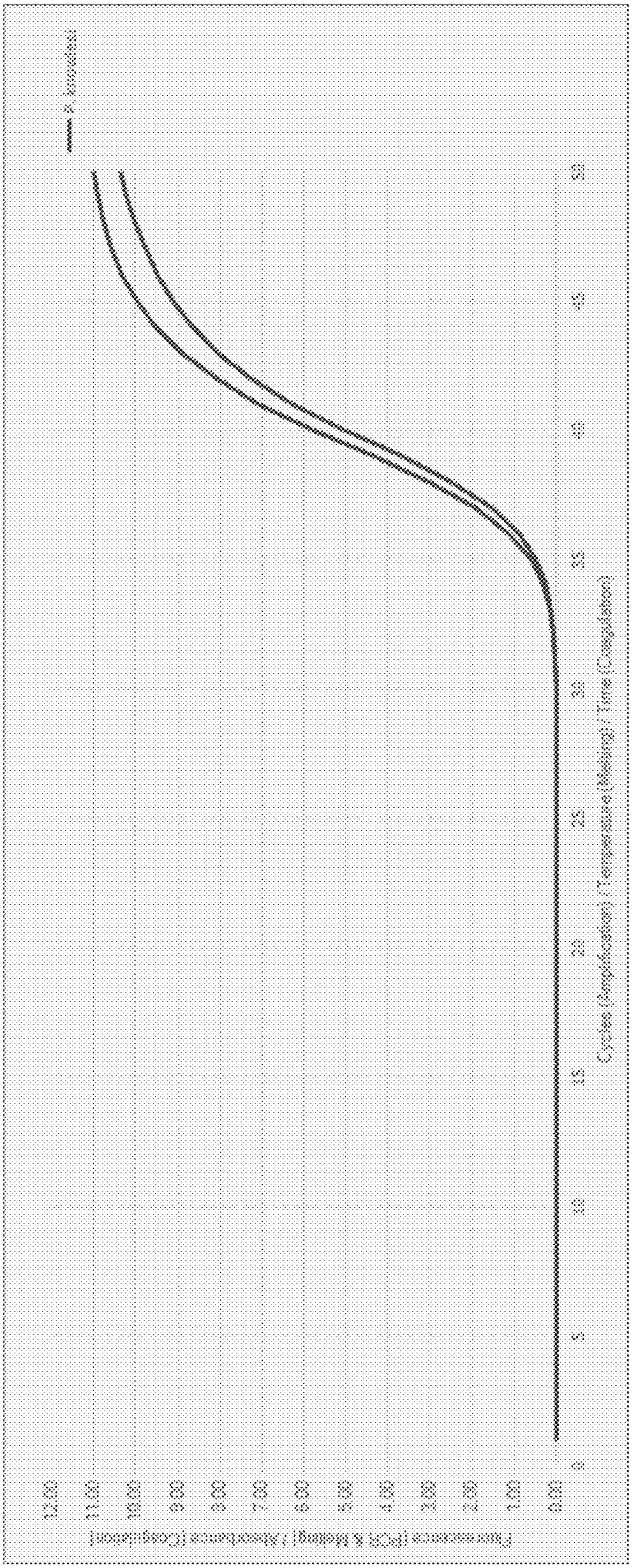
FIG. 13 shows the real time PCR growth curves from the multiplex assay with primers and probes for the 18S-1 and 18S-3 targets, using DNA plasmids containing the *P. knowlesi* 18S rRNA sequence at 1000 copies per PCR reaction level. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and probe having a nucleic acid sequence of SEQ ID NO:58.

Example 10: Multiplex Amplification and Detection of 18S-1 and 18S-3 Targets in *P. knowlesi* 18S rRNA Sequences by Real-Time PCR A multiplex assay was designed and developed to simultaneously amplify and detect the two targets with the 18S rRNA region (18S-1 and 18S-3) (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested against DNA plasmids containing *P. knowlesi* 18S rRNA sequence at 1,000 copies per PCR reaction level. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and a probe having a nucleic acid sequence of SEQ ID NO:58. The 18S-1 and 18S-3 targets were run in the FAM channel and the internal control (GIC) was run on the Cy5.5 channel. The results of this 18S-1 and 18S-3 multiplex Malaria assay are shown in FIG. 13. These results show that the multiplex assay effectively and simultaneously amplifies and detects the 18S-1 and 18S-3 targets of DNA plasmids containing *P. knowlesi* 18S rRNA sequence.

These studies demonstrate that the dual target multiplex assay can successfully and effectively simultaneously amplify and detect the 18S rRNA (18S-1 and 18S-3 targets) region of *Plasmodium.*

Figure 14:
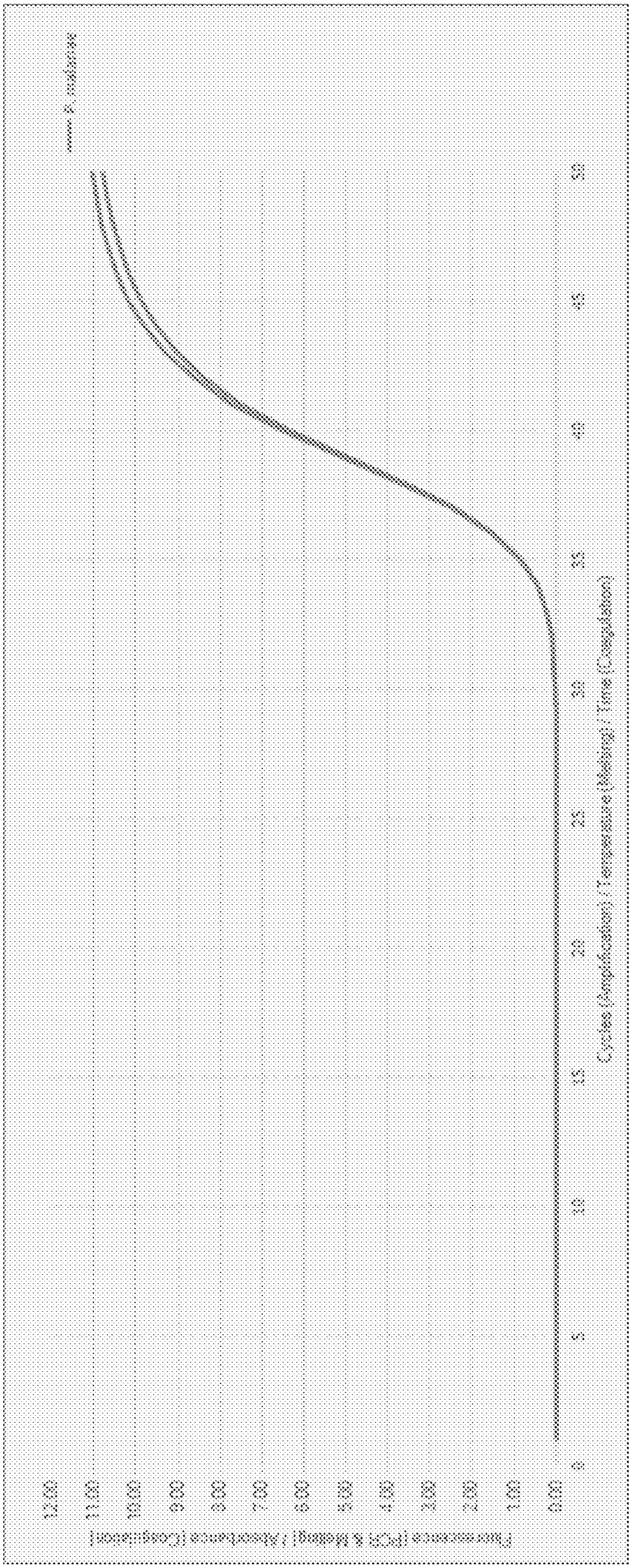
FIG. 14 shows the real time PCR growth curves from the multiplex assay with primers and probes for the 18S-1 and 18S-3 targets, using DNA plasmids containing the *P. malariae* 18S rRNA sequence at 1000 copies per PCR reaction level. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and probe having a nucleic acid sequence of SEQ ID NO:58.

Example 11: Multiplex Amplification and Detection of 18S-1 and 18S-3 Targets in *P. malariae* 18S rRNA Sequences by Real-Time PCR A multiplex assay was designed and developed to simultaneously amplify and detect the two targets with the 18S rRNA region (18S-1 and 18S-3) (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested against DNA plasmids containing *P. malariae* 18S rRNA sequence at 1,000 copies per PCR reaction level. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and a probe having a nucleic acid sequence of SEQ ID NO:58. The 18S-1 and 18S-3 targets were run in the FAM channel and the internal control (GIC) was run on the Cy5.5 channel. The results of this 18S-1 and 18S-3 multiplex Malaria assay are shown in FIG. 14. These results show that the multiplex assay effectively and simultaneously amplifies and detects the 18S-1 and 18S-3 targets of DNA plasmids containing *P. malariae* 18S rRNA sequence.

These studies demonstrate that the dual target multiplex assay can successfully and effectively simultaneously amplify and detect the 18S rRNA (18S-1 and 18S-3 targets) region of *Plasmodium*.

Figure 15:
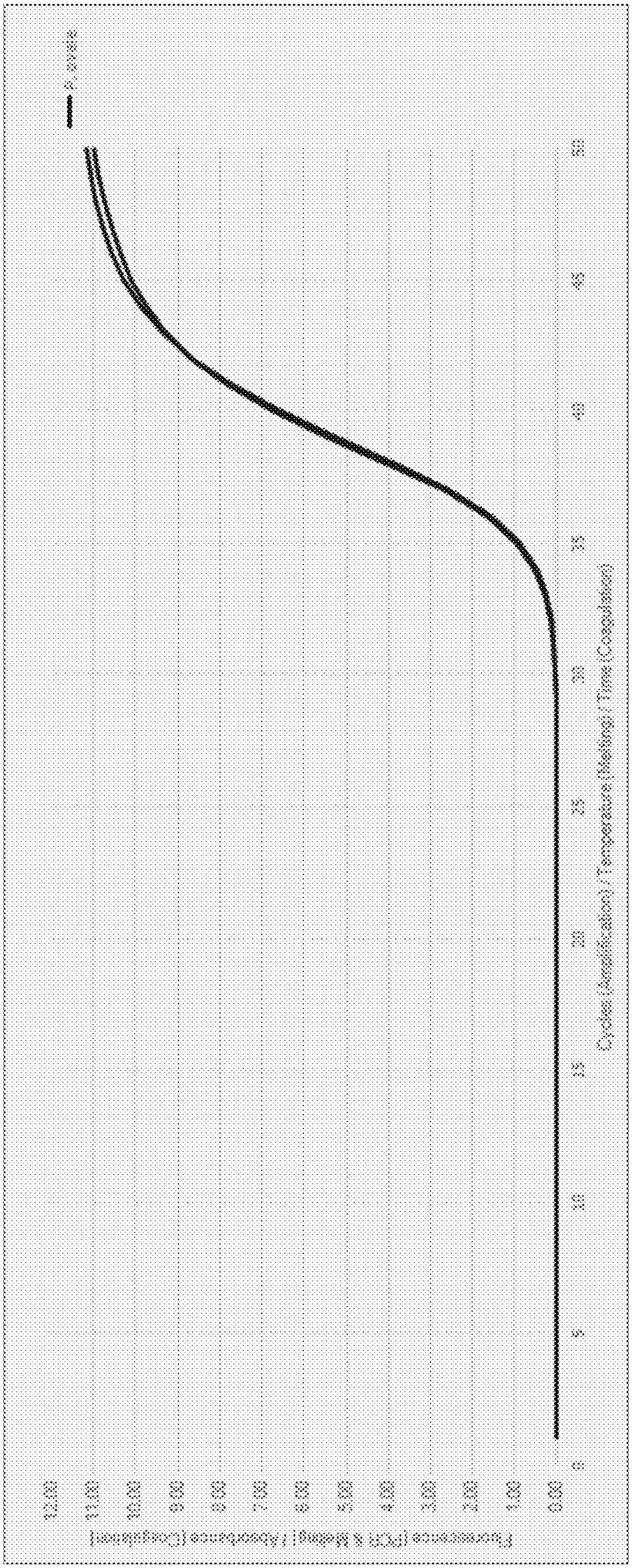
FIG. 15 shows the real time PCR growth curves from the multiplex assay with primers and probes for the 18S-1 and 18S-3 targets, using DNA plasmids containing the *P. ovale* 18S rRNA sequence at 1000 copies per PCR reaction level. For the 18S-1 target, this multiplex assay employed the primers having a nucleic acid sequence of SEQ ID NOs: 34-36, and probe having a nucleic acid sequence of SEQ ID NO:4. For the 18S-3 target, this multiplex assay employed the primers having a nucleic acid sequence of SEQ ID NOs:56 and 57, and probe having a nucleic acid sequence of SEQ ID NO:58.

Example 12: Multiplex Amplification and Detection of 18S-1 and 18S-3 Targets in *P. ovale* 18S rRNA Sequences by Real-Time PCR A multiplex assay was designed and developed to simultaneously amplify and detect the two targets with the 18S rRNA region (18S-1 and 18S-3) (i.e., duplex) within the same sample. In general, detection of multiple copy targets in parallel allows for increased sensitivity, and also mitigates the risk of any one singleplex assay failing by covering multiple targets. For example, if there are sequence variants, in, for example the 18S sequence, the risk of failure to detect the 18S sequence variant with the existing primer/probe set is mitigated by the presence of another set of primer/probe that detects a second separate target. This is the chief advantage of a multiplex assay over a singleplex assay. In this example, this multiplex assay was tested against DNA plasmids containing *P. ovale* 18S rRNA sequence at 1,000 copies per PCR reaction level. Reagents used include Cobas® 6800/8800 generic PCR Master Mix, with the profile and conditions for use with the Cobas® 6800/8800, and using TaqMan® amplification and detection technology. The final concentration of oligonucleotides in the master mix was 0.3 μM for primers and 0.2 μM for probes. The Cobas® 6800/8800 PCR Profile employed is shown in Table 2, above. For the 18S-1 target, this multiplex assay employed the primers having a nucleic acid sequence of SEQ ID NOs:34-36, and probe having a nucleic acid sequence of SEQ ID NO:4. For the 18S-3 target, this multiplex assay employed the primers having a nucleic acid sequence of SEQ ID NOs:56 and 57, and a probe having a nucleic acid sequence of SEQ ID NO:58. The 18S-1 and 18S-3 targets were run in the FAM channel and the internal control (GIC) was run on the Cy5.5 channel. The results of this 18S-1 and 18S-3 multiplex Malaria assay are shown in FIG. 15. These results show that the multiplex assay effectively and simultaneously amplifies and detects the 18S-1 and 18S-3 targets of DNA plasmids containing *P. ovale* 18S rRNA sequence.

These studies demonstrate that the dual target multiplex assay can successfully and effectively simultaneously amplify and detect the 18S rRNA (18S-1 and 18S-3 targets) region of *Plasmodium*. In particular, Examples 8-12 demonstrate that the multiplex assay targeting the 18S-1 and 18S-3 specifically and efficiently amplify and detect Malaria parasites (including *Plasmodium*, which includes *P. falciparum, P. vivax, P. ovale, P. knowlesi*, and *P. malariae*), with the oligonucleotides for the 18S-1 target having primers having a nucleic acid sequence of SEQ ID NOs:34-36, and probe having a nucleic acid sequence of SEQ ID NO:4, and with the oligonucleotides for the 18S-3 target having primers having a nucleic acid sequence of SEQ ID NOs:56 and 57, and probe having a nucleic acid sequence of SEQ ID NO:58.

Thus, taken together, these results demonstrate that the oligonucleotide set of SEQ ID NOs:1-58 specifically and efficiently amplify and detect Malaria parasites (including *Plasmodium*, which includes *P. falciparum, P. vivax, P. ovale, P. knowlesi*, and *P. malariae*), in whole blood.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, the sequence listing and/or other documents cited in this application are incorporated by reference in their entirety for all purposes to the same extent as if each individual publication, patent, patent application, the sequence listing and/or other document were individually indicated to be incorporated by reference for all purposes.

The invention claimed is:

1. A method for detecting one or more Malaria parasite species in a sample, the method comprising:

(a) performing an amplification step comprising contacting the sample with one or more set of primers to produce an amplification product, if a target nucleic acid of the one or more Malaria parasite species is present in the sample;

(b) performing a hybridization step comprising contacting the one or more probes with the amplification product, if a target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises:

(1) primers comprising the nucleic acid sequences of SEQ ID NOs: 34, 35, and 36; and a probe comprising the nucleic acid sequence of SEQ ID NO: 4, or a complement thereof; and/or (2) primers comprising the nucleic acid sequence of SEQ ID NOs: 56 and 57; and a probe comprising the nucleic acid sequence of SEQ ID NO: 58, or a complement thereof.

2. The method of claim 1, wherein the one or more set of primers and the one or more probes comprises:

(1) primers comprising the nucleic acid sequences of SEQ ID NOs: 34, 35, and 36; and a probe comprising the nucleic acid sequence of SEQ ID NO: 4, or a complement thereof; and (2) primers comprising the nucleic acid sequence of SEQ ID NOs: 56 and 57; and a probe comprising the nucleic acid sequence of SEQ ID NO: 58, or a complement thereof.

3. The method of claim 1, wherein the one or more Malaria parasite species belongs to the genus *Plasmodium.*

4. The method of claim 3, wherein the one or more Malaria parasite species that belongs to the genus *Plasmodium* is *P. falciparum, P. vivax, P. ovale, P. malariae*, and/or *P. knowlesi.*

5. The method of claim 1, wherein the sample is a biological sample.

6. The method of claim 5, wherein the biological sample is whole blood, respiratory specimens, urine, fecal specimens, blood specimens, plasma, dermal swabs, nasal swabs, wound swabs, blood cultures, skin, or soft tissue infections.

7. The method of claim 6, wherein the biological sample is whole blood.

8. The method of claim 1, wherein the one or more probes is labeled.

9. The method of claim 8 wherein the one or more probes is labeled with a donor fluorescent moiety and a corresponding acceptor moiety.

10. The method of claim 9, wherein step (c) further comprises detecting the presence or absence of fluorescent resonance energy transfer (FRET) between the donor fluorescent moiety and the acceptor moiety of the one or more probes, wherein the presence or absence of fluorescence is indicative of the presence of absence of the one or more Malaria parasite species in the sample.

11. A method for detecting a first target nucleic acid and/or a second target nucleic acid of one or more Malaria parasite species in a sample, the method comprising:

(a) performing an amplification step comprising contacting the sample with one or more set of primers to produce an amplification product, if the first target nucleic acid and/or the second target nucleic acid of the one or more Malaria parasite species is present in the sample;

(b) performing a hybridization step comprising contacting the one or more probes with the amplification product, if the first target nucleic acid and/or the second target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises:

(1) a set of primers and a probe for the first target nucleic acid of the one or more Malaria parasite species, wherein the set of primers comprises primers comprising the nucleic acid sequences of SEQ ID NOs: 34, 35, and 36; and wherein the probe comprises the nucleic acid sequence of SEQ ID NO:4, or a complement thereof; and (2) a set of primers and a probe for the second target nucleic acid of the one or more Malaria parasite species, wherein the set of primers comprises primers comprising the nucleic acid sequences of SEQ ID NOs: 56 and 57; and wherein the probe comprises the nucleic acid sequence of SEQ ID NO:58, or a complement thereof.

12. A method for detecting one or more Malaria parasite species in a sample, the method comprising:

(a) performing an amplification step comprising contacting the sample with one or more set of primers to produce an amplification product, if a target nucleic acid of the one or more Malaria parasite species is present in the sample;

(b) performing a hybridization step comprising contacting the one or more probes with the amplification product, if the target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises primers comprising the nucleic acid sequences of SEQ ID NOs: 34, 35, and 36; and a probe comprising the nucleic acid sequence of SEQ ID NO:4.

13. A method for detecting one or more Malaria parasite species in a sample, the method comprising:

(a) performing an amplification step comprising contacting the sample with one or more set of primers to produce an amplification product, if a target nucleic acid of the one or more Malaria parasite species is present in the sample;

(b) performing a hybridization step comprising contacting the one or more probes with the amplification product, if the target nucleic acid of the one or more Malaria parasite species is present in the sample; and (c) detecting the presence or absence of the amplification product, wherein the presence of the amplification product is indicative of the presence of the one or more Malaria parasite species in the sample, and wherein the absence of the amplification product is indicative of the absence of the one or more Malaria parasite species in the sample; and wherein the one or more set of primers and the one or more probes comprises a primers comprising the nucleic acid sequences of SEQ ID NOs: 56 and 57, or complements thereof, and a probe comprising the nucleic acid sequence of SEQ ID NO:58, or a complement thereof.

14. The method of any one of claims 11-13, wherein the one or more Malaria parasite species belongs to the genus *Plasmodium*.

15. The method of claim 14, wherein the one or more Malaria parasite species that belongs to the genus *Plasmodium* is *P. falciparum, P. vivax, P. ovale, P. malariae*, and/or *P. knowlesi*.

16. The method of any one of claims 11-13, wherein the sample is a biological sample.

17. The method of claim 16, wherein the biological sample is whole blood, respiratory specimens, urine, fecal specimens, blood specimens, plasma, dermal swabs, nasal swabs, wound swabs, blood cultures, skin, or soft tissue infections.

18. The method of claim 17, wherein the biological sample is whole blood.

19. The method of any one of claims 11-13, wherein the one or more probes is labeled.

20. The method of claim 19 wherein the one or more probes is labeled with a donor fluorescent moiety and a corresponding acceptor moiety.

* * * * *

SEQUENCE LISTING

```
<160> NUMBER OF SEQ ID NOS: 58

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1

ggagcctgag aaatagctac cac                                   23
```

<210> SEQ ID NO 2
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 2
tttcttgtca ctacctctct tctttagaa 29

<210> SEQ ID NO 3
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 3
aaggaaggca gcaggcgcgt aaattaccc 29

<210> SEQ ID NO 4
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 4
aggcagcagg cgcgtaaatt acccaa 26

<210> SEQ ID NO 5
<211> LENGTH: 16
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 5
cggaagggca ccacca 16

<210> SEQ ID NO 6
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 6
atctgtcaat cctactcttg tcttaaacta 30

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 7
tggagcttgc ggcttaattt gactcaacac gg 32

<210> SEQ ID NO 8
<211> LENGTH: 30
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 8
acaagagtag gattgacaga ttaatagctc 30

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 9
cgttatcgga attaaccaga caaatcata 29

<210> SEQ ID NO 10
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 10
tggatggtga tgcatggccg tttttagttc gt 32

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 11
acaggttaac gcctggagtt c 21

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 12
tgtcgtctca tcgcagcc 18

<210> SEQ ID NO 13
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 13
gcacctccat gtcgtctca 19

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 14
tctttatata ctattggcac ctccatgtc 29

<210> SEQ ID NO 15
<211> LENGTH: 28
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 15
cgtgacgagc ggtgtgtaca aggcaaca 28

<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
tctgcccggc atcaatgata aa 22

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
ggagtctcac actagcgaca a 21

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 18
ccttgtcggg taatctccgt cctgcatgaa cg 32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 19
ccttgtcggg taatctccgt cctgcatgaa cg 32

<210> SEQ ID NO 20

<211> LENGTH: 32
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 20
ccttgtcggg taatctccgt cctgcatgaa cg 32

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 21
ttctgcgtcc caatgatagg aa 22

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 22
ggcctatcga tcctttatat ttgca 25

<210> SEQ ID NO 23
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 23
acgtcgctag gagcgcttgg cagc 24

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 24
acgtcgctag gagcgcttgg cagc 24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 25
acgtcgctag gagcgcttgg cagc 24

<210> SEQ ID NO 26
<211> LENGTH: 23

<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 26
tgaacaatcc gacactttga gac 23

<210> SEQ ID NO 27
<211> LENGTH: 23
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 27
tgaacaatcc gacactttga gac 23

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 28
gccacgcttt cacgttttc 19

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 29
cggtacatct gttaaaaaat aacgca 26

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<223> OTHER INFORMATION: Description of Combined DNA/RNA Molecule:
Synthetic oligonucleotide

<400> SEQUENCE: 30
agauuuctgt tctctttgag cttgtctttg gacat 35

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
gggtattggc ctaacatggc ta 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 32
gggtattgac ctaacatggc ta 22

<210> SEQ ID NO 33
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 33
tttcttgtca ctacctctct tctttaga 28

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 34
ggtattggcc taacatggct atga 24

<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 35
ggtattgacc taacatggct atga 24

<210> SEQ ID NO 36
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 36
tttcttgtca ctacctctct tctttagaa 29

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 37
aaggaaggca gcaggcgcgt aaattaccc 29

<210> SEQ ID NO 38

<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 38
tggagcttgc ggcttaattt gactcaacac gg 32

<210> SEQ ID NO 39
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 39
tggatggtga tgcatggccg tttttagttc gt 32

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 40
acgtcgctag gagcgcttgg cagc 24

<210> SEQ ID NO 41
<211> LENGTH: 28
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 41
cgtgacgagc ggtgtgtaca aggcaaca 28

<210> SEQ ID NO 42
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 42
ccttgtcggg taatctccgt cctgcatgaa cg 32

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 43
ggcctatcga tatcctttat gtttgc 26

<210> SEQ ID NO 44
<211> LENGTH: 10

<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 44
aaggaaggca 10

<210> SEQ ID NO 45
<211> LENGTH: 19
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 45
gcaggcgcgt aaattaccc 19

<210> SEQ ID NO 46
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 46
tggagcttgc 10

<210> SEQ ID NO 47
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 47
ggcttaattt gactcaacac gg 22

<210> SEQ ID NO 48
<211> LENGTH: 10
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 48
tggatggtga 10

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 49
tgcatggccg tttttagttc gt 22

<210> SEQ ID NO 50
<211> LENGTH: 10
<212> TYPE: DNA

```
<213> ORGANISM: Artificial Sequence
<220> FEATURE:
<223> OTHER INFORMATION: Description of Artificial Sequence: Synthetic
      oligonucleotide

<400> SEQUENCE: 50

acgtcgctag                                                            10


<210> SEQ ID NO 51
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51

gagcgcttgg cagc                                                       14


<210> SEQ ID NO 52
<211> LENGTH: 9
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52

cgtgacgag                                                              9


<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53

cggtgtgtac aaggcaaca                                                  19


<210> SEQ ID NO 54
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54

ccttgtcggg                                                            10


<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 55

taatctccgt cctgcatgaa cg                                              22


<210> SEQ ID NO 56
<211> LENGTH: 25
<212> TYPE: DNA
<213> ORGANISM: Artificial Sequence
```

-continued

```
<220> FEATURE:
<223> OTHER INFORMATION: Description of Artificial Sequence: Synthetic
      oligonucleotide

<400> SEQUENCE: 56

caacacggga aaactcacta gttta                                            25


<210> SEQ ID NO 57
<211> LENGTH: 28
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 57

accagacaaa tcatattcac gaactaaa                                         28


<210> SEQ ID NO 58
<211> LENGTH: 29
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 58

tgauutcttg gatggtgatg catggccgt                                        29
```